(12) United States Patent
Kawamura

(10) Patent No.: US 10,781,808 B2
(45) Date of Patent: Sep. 22, 2020

(54) VALVE, FLUID CONTROL DEVICE, AND SPHYGMOMANOMETER

(71) Applicant: Murata Manufacturing Co., Ltd., Kyoto (JP)

(72) Inventor: Kenichiro Kawamura, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 674 days.

(21) Appl. No.: 15/491,405

(22) Filed: Apr. 19, 2017

(65) Prior Publication Data

US 2017/0215744 A1     Aug. 3, 2017

Related U.S. Application Data

(63) Continuation of application No. PCT/JP2015/078139, filed on Oct. 5, 2015.

(30) Foreign Application Priority Data

Oct. 21, 2014   (JP) .................................. 2014-214553

(51) Int. Cl.
*F04B 43/04*    (2006.01)
*F04B 53/10*    (2006.01)
(Continued)

(52) U.S. Cl.
CPC .......... *F04B 43/043* (2013.01); *F04B 43/046* (2013.01); *F04B 53/106* (2013.01);
(Continued)

(58) Field of Classification Search
CPC .... F04B 43/046; F04B 43/043; F04B 45/047; F04B 53/106; F16K 7/17
See application file for complete search history.

(56) References Cited

U.S. PATENT DOCUMENTS 1,048,502 A  *  12/1912  Deimling ............... B61D 23/02
                                                    105/448
8,905,940 B2 *  12/2014  Sano ..................... A61B 5/0235
                                                    600/498
(Continued)

FOREIGN PATENT DOCUMENTS

JP     2-033975 U      3/1990
JP     2001-173569 A   6/2001
(Continued)

OTHER PUBLICATIONS

International Search Report issued in Application No. PCT/JP2015/078139 dated Dec. 28, 2015.
(Continued)

*Primary Examiner* — Peter J Bertheaud
(74) *Attorney, Agent, or Firm* — Pearne & Gordon LLP

(57) ABSTRACT

A sphygmomanometer device includes a piezoelectric pump, a valve, and a cuff. The valve includes a first valve housing, a diaphragm, and a second valve housing. The diaphragm is fixed to the second valve housing and first valve housing such that it is separated from a valve seat and the periphery of an opening portion in the diaphragm is in contact with a valve seat while providing a pressure thereto. Thus, the diaphragm defines a lower valve chamber communicating with a first vent hole, an upper valve chamber communicating with a second vent hole, a lower valve chamber communicating with a first vent hole, and an upper valve chamber communicating with the upper valve chamber, together with the second valve housing and first valve housing.

8 Claims, 19 Drawing Sheets

(51) Int. Cl.
*F16K 7/17* (2006.01)
*F04B 45/047* (2006.01)
*F04B 53/06* (2006.01)

(52) U.S. Cl.
CPC ............... *F16K 7/17* (2013.01); *F04B 43/04* (2013.01); *F04B 45/047* (2013.01); *F04B 53/06* (2013.01); *F04B 53/1087* (2013.01)

(56) References Cited

U.S. PATENT DOCUMENTS

| | | | |
|---|---|---|---|
| 9,033,683 B2 * | 5/2015 | Kodama | ............... A61B 5/0235 |
| | | | 137/510 |
| 9,237,845 B2 * | 1/2016 | Numajiri | ................. A61B 3/113 |
| 9,631,730 B2 * | 4/2017 | Kotani | ................... A61B 5/022 |
| 9,951,879 B2 * | 4/2018 | Kotani | ................... F16K 31/128 |
| 10,350,337 B2 * | 7/2019 | Kurihara | ............. A61M 1/0066 |
| 2015/0034847 A1 | 2/2015 | Kotani | |

FOREIGN PATENT DOCUMENTS

| | | | | |
|---|---|---|---|---|
| JP | 2014-077384 A | 5/2014 | | |
| WO | 2013/157304 A1 | 10/2013 | | |
| WO | WO 2013157304 A1 * | 10/2013 | ............ | F04B 43/043 |

OTHER PUBLICATIONS

Written Opinion issued in Application No. PCT/JP2015/078139 dated Dec. 28, 2015.
Inoue Tatsuo, "Dansei Rikigaku No Kiso (Fundamentals of Elastodynamics)", Nikkan Kogyo Shimbun Ltd., Mar. 1979. Cited in the Specification on p. 32.

* cited by examiner

VALVE, FLUID CONTROL DEVICE, AND SPHYGMOMANOMETER

This is a continuation of International Application No. PCT/JP2015/078139 filed on Oct. 5, 2015 which claims priority from Japanese Patent Application No. 2014-214553 filed on Oct. 21, 2014. The contents of these applications are incorporated herein by reference in their entireties.

BACKGROUND

Technical Field

The present disclosure relates to a valve that prevents backflow of fluid, a fluid control device that includes the valve, and a sphygmomanometer that includes the fluid control device.

Patent Document 1 discloses a fluid control device that includes a valve.

FIG. 17 is a cross-sectional view of a main portion in a fluid control device 900 according to Patent Document 1. The fluid control device 900 includes a piezoelectric pump 10, a valve 901, and a cuff 109.

The fluid control device 900 is a device for measuring blood pressure of a subject. The upper surface of the piezoelectric pump 10 is joined to the bottom surface of the valve 901, and thus the valve 901 is connected to the piezoelectric pump 10. The valve 901 has a cuff connection port 106A connected to the cuff 109. The cuff 109 is a flexible container that can store air. The details of the piezoelectric pump 10 are described below.

As illustrated in FIG. 17, the valve 901 includes a first valve housing 991, a diaphragm 920 made of a thin film having a substantially rectangular shape, and a second valve housing 992.

The first valve housing 991 has a first vent hole 910 communicating with a discharge hole 56 in the piezoelectric pump 10, a first vent hole 911 communicating with a discharge hole 55 in the piezoelectric pump 10, and a valve seat 938 having a substantially columnar shape and protruding toward the diaphragm 920.

The second valve housing 992 has a second vent hole 912 communicating with the cuff 109, a third vent hole 913 communicating with the outside of the fluid control device 900, and a valve seat 939 protruding from the periphery of the third vent hole 913 toward the diaphragm 920. The valve seat 939 has a substantially cylindrical shape having the third vent hole 913 in its central portion.

The diaphragm 920 has a circular opening portion 921 in the central portion of an area opposed to the valve seat 938. The diaphragm 920 is held between (fixed to) the second valve housing 992 and first valve housing 991 such that part of the diaphragm 920 is in contact with the valve seat 939 while providing a pressure thereto and the periphery of the opening portion 921 in the diaphragm 920 is in contact with the valve seat 938 while providing a pressure thereto.

Thus, the diaphragm 920 partitions the inside of the second valve housing 992 and first valve housing 991. The diaphragm 920 defines a lower valve chamber 931 communicating with the first vent hole 911 and an upper valve chamber 933 communicating with the second vent hole 912 with a communication path 135 interposed therebetween, together with the second valve housing 992 and first valve housing 991.

The diaphragm 920 defines a lower valve chamber 932 communicating with the first vent hole 910 and an upper valve chamber 934 communicating with the upper valve chamber 933 with the communication path 135 interposed therebetween, together with the second valve housing 992 and first valve housing 991.

Next, operations of the fluid control device 900 in blood pressure measurement are described.

FIG. 18 is an explanatory drawing of an air stream in the fluid control device 900 while the piezoelectric pump 10 illustrated in FIG. 17 is driven. FIG. 19 is an explanatory drawing of an air stream in the fluid control device 900 immediately after the piezoelectric pump 10 illustrated in FIG. 17 is deactivated. FIG. 20 illustrates pressure changes in the upper valve chamber 934 included in the valve 901 illustrated in FIG. 17 and pressure changes in the lower valve chamber 932.

To start blood pressure measurement, first, the fluid control device 900 activates the piezoelectric pump 10. When the piezoelectric pump 10 is activated, first, air flows into a pump chamber 45 inside the piezoelectric pump 10 through an opening portion 92 and a suction hole 52. Next, the air is discharged through the discharge holes 55 and 56 and flows into both the lower valve chambers 932 and 931 in the valve 901.

Thus, in an exhaust valve 170, a pressure P2 in the lower valve chamber 932 becomes higher than a pressure P1 in the upper valve chamber 934 (see FIG. 20). Because of this, as illustrated in FIG. 18, the diaphragm 920 seals the third vent hole 913 and interrupts communication between the second vent hole 912 and third vent hole 913.

In a check valve 160, the pressure P2 in the lower valve chamber 931 becomes higher than the pressure P1 in the upper valve chamber 933 (see FIG. 20). Because of this, the periphery of the opening portion 921 in the diaphragm 920 becomes separated from the valve seat 938, and the first vent hole 911 and second vent hole 912 are made to communicate with each other with the opening portion 921 interposed therebetween.

Consequently, the air is sent from the piezoelectric pump 10 through the first vent hole 911, the opening portion 921, and the second vent hole 912 in the valve 901 to the cuff 109 (see FIG. 18), and this leads to an increased pressure (air pressure) inside the cuff 109.

Next, an air stream in the fluid control device 900 immediately after the piezoelectric pump 10 is deactivated is described.

When blood pressure measurement ends, the fluid control device 900 deactivates the piezoelectric pump 10. When the piezoelectric pump 10 is deactivated, the air in the pump chamber 45, lower valve chamber 931, and lower valve chamber 932 is quickly exhausted to the outside of the fluid control device 900 through the suction hole 52 and opening portion 92 in the piezoelectric pump 10. The upper valve chamber 933 and upper valve chamber 934 receive the pressure in the cuff 109 through the second vent hole 912.

Consequently, in the check valve 160, the pressure P2 in the lower valve chamber 932 becomes lower than the pressure P1 in the upper valve chamber 934. The diaphragm 920 comes into contact with the valve seat 938, and the opening portion 921 is sealed.

In the exhaust valve 170, the pressure P2 in the lower valve chamber 932 becomes lower than the pressure P1 in the upper valve chamber 934. The diaphragm 920 becomes separated from the valve seat 939 and opens the third vent hole 913.

That is, in the valve 901, the second vent hole 912 and third vent hole 913 communicate with each other with the communication path 135 and upper valve chamber 934 interposed therebetween. Thus, the air in the cuff 109 is quickly exhausted out from the third vent hole 913 through the second vent hole 912, communication path 135, and upper valve chamber 934 (see FIG. 19).

Accordingly, the valve 901 in Patent Document 1 can enable filling the cuff 109 with compressed air and then quickly exhausting the air from the cuff 109 (see FIG. 20). Thus, the cuff 109 quickly shrinks, and the fluid control device 900 becomes ready to carry out next blood pressure measurement at once.

Patent Document 1: International Publication No. 2013-157304

BRIEF SUMMARY

The present inventor conducted a study below to improve the accuracy of blood pressure measurement with the valve 901 in Patent Document 1.

As illustrated in FIG. 17, the diaphragm 920 and valve seat 939 are not separated from each other, and the diaphragm 920 is in contact with (provides a pressure to) the valve seat 939. Because of this, a valve opening pressure P5 equal to or higher than the provided pressure is needed to separate the diaphragm 920 from the valve seat 939.

Hence, as illustrated in FIG. 20, after the piezoelectric pump 10 is deactivated, when the air is exhausted from the cuff 109 and the pressure P1 in the upper valve chamber 934 reaches the valve opening pressure P5, the diaphragm 920 moves from an open state to a state in which it closes the third vent hole 913 in the valve seat 939.

That is, before the air inside the cuff 109 is fully exhausted (specifically, before the pressure inside the cuff 109 reaches atmospheric pressure), the diaphragm 920 closes the third vent hole 913 in the valve seat 939. Consequently, the pressure inside the cuff 109 and the pressure in the upper valve chamber 934 remain at the valve opening pressure P5.

Hence, with the valve 901 in Patent Document 1, an error corresponding to the amount of pressure remaining inside the cuff 109 occurs in next blood pressure measurement. Accordingly, for the valve 901 in Patent Document 1, it is necessary to correct the error in blood pressure measurement every time.

The present disclosure provides a valve, a fluid control device, and a sphygmomanometer capable of filling a container with compressed gas and capable of exhausting the gas from the container until the pressure inside the container reaches atmospheric pressure.

A valve according to the present disclosure includes a valve housing and a diaphragm. The valve housing has a first vent hole, a second vent hole, a third vent hole, a first valve seat, and a second valve seat. The second valve seat protrudes from a periphery of the third vent hole.

The diaphragm has an opening portion and is fixed to the valve housing such that a periphery of the opening portion is in contact with the first valve seat while providing a pressure thereto and the diaphragm is separated from the second valve seat. The diaphragm defines a first valve chamber communicating with the first vent hole and a second valve chamber communicating with the second vent hole and the third vent hole, together with the valve housing.

When a pressure in the first valve chamber is higher than a pressure in the second valve chamber and lower than the provided pressure, the diaphragm is in contact with the second valve seat and closes the third vent hole. When the pressure in the first valve chamber is equal to or higher than the provided pressure, the diaphragm is separated from the first valve seat.

In this configuration, for example, the first vent hole in the valve is connected to a discharge hole in a pump, the second vent hole in the valve is connected to a container, and the third vent hole in the valve is opened to the atmosphere.

In this configuration, when the pump is activated, gas flows from the discharge hole in the pump through the first vent hole into the first valve chamber. Thus, the pressure in the first valve chamber gradually increases. After the pressure in the first valve chamber becomes higher than the pressure in the second valve chamber and lower than the provided pressure, it becomes equal to or higher than the provided pressure.

Because of this, in this configuration, the diaphragm closes the third vent hole and then becomes separated from the first valve seat. Thus, the gas flowing into the first valve chamber flows into the second valve chamber through the opening portion and flows into the container through the second vent hole. Consequently, the container is filled with compressed gas.

Next, when the pump is deactivated and the pressure in the first valve chamber becomes equal to or lower than the pressure in the second valve chamber, the diaphragm returns to an original state. That is, the diaphragm comes into contact with the first valve seat and becomes separated from the second valve seat. Consequently, the compressed gas in the container is quickly exhausted through the second vent hole and third vent hole.

At this time, because the diaphragm is fixed to the valve housing such that it is separated from the second valve seat, it does not close the third vent hole. That is, the valve having the above-described configuration is maintained in a state where the second vent hole and third vent hole communicate with each other. Because of this, the valve having the above-described configuration can enable the gas inside the container to be fully exhausted until the pressure inside the container reaches atmospheric pressure.

Accordingly, the valve having the above-described configuration can enable the container to be filled with the compressed gas and can enable the gas to be exhausted from the container until the pressure inside the container reaches atmospheric pressure.

The relationship $w=3/16\times((1-v^2)/(E\times t^3))\times P\times(r^2-a^2)^2$ is satisfied, where E denotes the Young's modulus of the diaphragm, v denotes the Poisson's ratio of the diaphragm, a denotes the radius of the portion receiving a pressure in the first valve chamber in the diaphragm, t denotes the thickness of the diaphragm, r denotes the distance from the central axis of the diaphragm to the outermost peripheral point in the perimeter of the third vent hole, and w denotes the swelling amount at a location on the peripheral point axis in the diaphragm when the pressure difference P is applied.

The valve according to the present disclosure may satisfy the relationship $y<3/16\times((1-v^2)/(E\times t^3))\times P3\times(r^2-a^2)^2$, where P3 denotes the provided pressure, and y denotes the distance from a location on the peripheral point axis in the diaphragm to the second valve seat.

In the case where this relationship is satisfied, when the pressure in the first valve chamber is higher than the pressure in the second valve chamber and lower than the provided pressure, the diaphragm is in contact with the second valve seat and closes the third vent hole, and when the pressure in the first valve chamber is equal to or higher than the provided pressure, the diaphragm is separated from the first valve seat.

A fluid control device according to the present disclosure includes a pump having a discharge hole, the valve, and a container capable of storing fluid. The first vent hole in the valve is connected to the discharge hole in the pump. The second vent hole in the valve is connected to the container.

At the exhaust time, in which the diaphragm is separated from the second valve seat, vibration of the diaphragm produces an exhaust sound. As the valve opening pressure for the second valve seat increases (that is, the tension of the diaphragm increases), the vibration of the diaphragm increases and the exhaust sound increases.

In the valve having the above-described configuration, the valve opening pressure for the second valve seat is zero. Because of this, the valve having the above-described configuration can suppress an exhaust sound during the exhaust.

A sphygmomanometer according to the present disclosure includes the fluid control device according to the present disclosure.

With the above-described configuration, the fluid control device and sphygmomanometer including the valve according to the present disclosure can also offer substantially the same advantages.

According to the present disclosure, a container can be filled with compressed gas, and the gas can be exhausted from the container until the pressure inside the container reaches atmospheric pressure.

DETAILED DESCRIPTION

A sphygmomanometer device 100 according to a first embodiment of the present disclosure is described below.

Figure 1:
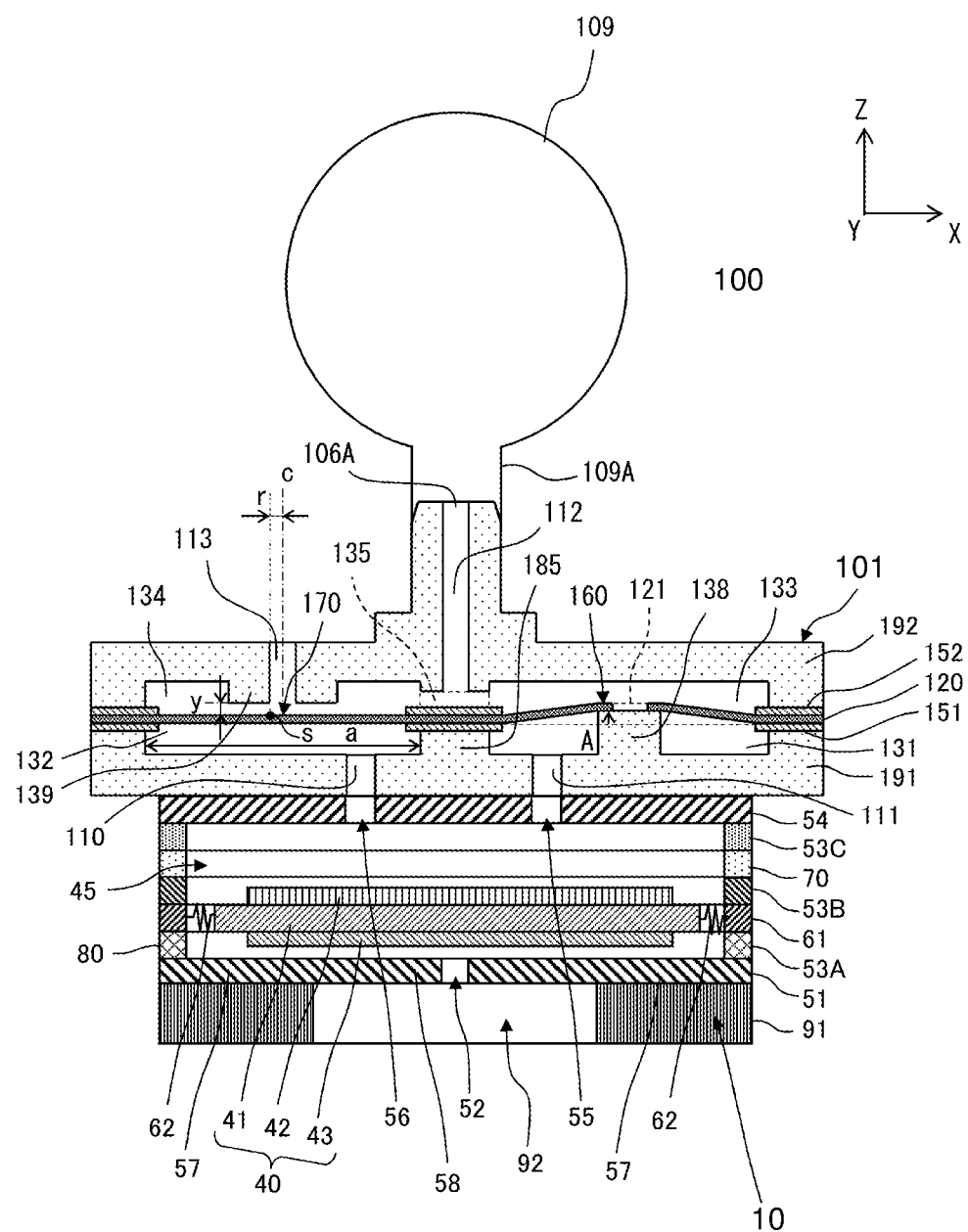
FIG. 1 is a cross-sectional view of a main portion in a sphygmomanometer device 100 according to a first embodiment of the present disclosure.

FIG. 1 is a cross-sectional view of a main portion in the sphygmomanometer device 100 according to the first embodiment of the present disclosure. The sphygmomanometer device 100 includes a piezoelectric pump 10, valve 101, and cuff 109. The sphygmomanometer device 100 is a device for measuring blood pressure of a subject. The upper surface of the piezoelectric pump 10 is joined to the bottom surface of the valve 101, and thus the valve 101 is connected to the piezoelectric pump 10.

The valve 101 has a cuff connection port 106A for connecting to a cuff rubber tube 109A in the cuff 109. The cuff rubber tube 109A in the cuff 109 is attached to the cuff connection port 106A in the valve 101, and thus the sphygmomanometer device 100 is connected to the cuff 109. The cuff 109 is a flexible container that can store air.

The cuff 109 corresponds to an example of a "container" in the present disclosure.

Here, the structures of the piezoelectric pump 10 and valve 101 are described. First, the structure of the piezoelectric pump 10 is described with reference to FIGS. 1 and 2.

Figure 2:
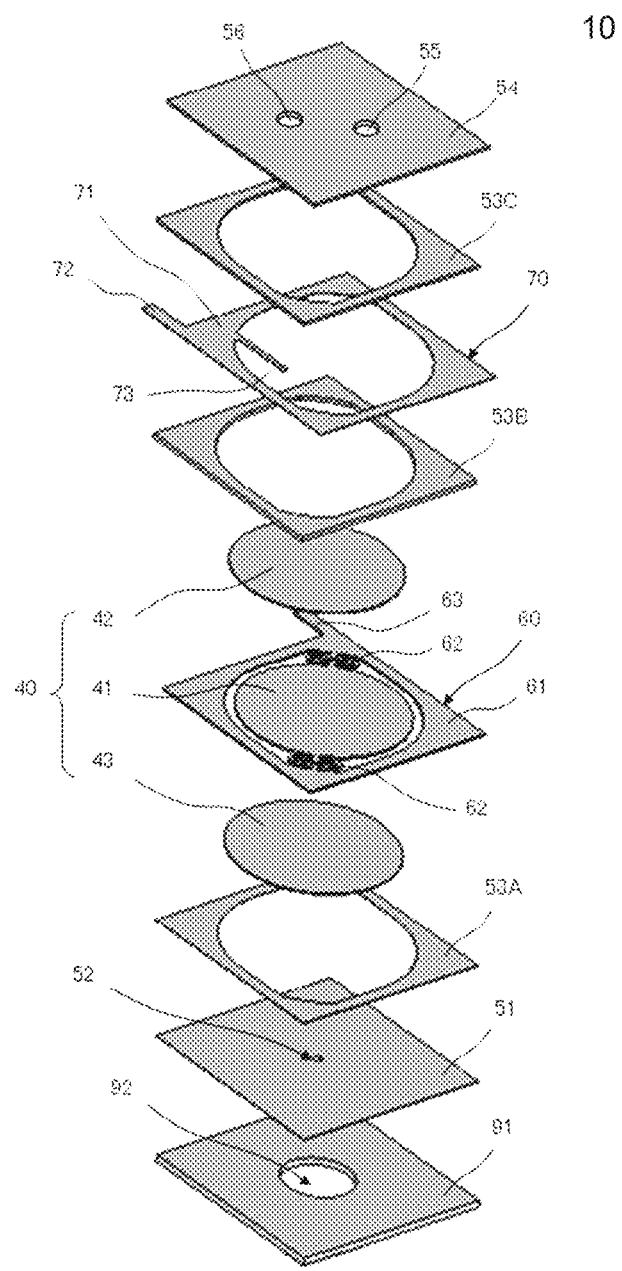
FIG. 2 is an exploded perspective view of a piezoelectric pump 10 illustrated in FIG. 1.

FIG. 2 is an exploded perspective view of the piezoelectric pump 10 illustrated in FIG. 1. The piezoelectric pump 10 includes a substrate 91, a flexible plate 51, a spacer 53A, a reinforcement 43, a vibrating plate unit 60, a piezoelectric element 42, a spacer 53B, an electrode conductive plate 70, a spacer 53C, and a cover plate 54 and has a structure in which they are laminated in sequence.

The substrate 91, flexible plate 51, spacer 53A, part of the vibrating plate unit 60, spacer 53B, electrode conductive plate 70, spacer 53C, and cover plate 54 constitute a pump housing 80. The inner space of the pump housing 80 corresponds to a pump chamber 45.

The vibrating plate unit 60 includes a vibrating plate 41, a frame plate 61, coupling portions 62, and an outer terminal 63. The vibrating plate unit 60 is formed by punching performed on a metal plate.

The frame plate 61 is disposed around the vibrating plate 41. The frame plate 61 is provided with the outer terminal 63 to be electrically connected. The vibrating plate 41 is coupled to the frame plate 61 with the coupling portions 62. One example of the coupling portions 62 may have a narrow annular shape. The coupling portions 62 have an elastic structure having elasticity of a small spring constant.

Accordingly, the vibrating plate 41 is elastically supported on the frame plate 61 at two points by the two coupling portions 62 in a flexible manner. Because of this, bending vibration of the vibrating plate 41 is not substantially hindered. That is, in this state, the peripheral portion (of course the central portion) of a piezoelectric actuator 40 is not virtually restrained.

The coupling portions 62 are disposed at two locations in the example illustrated in FIG. 2. The coupling portions 62 may be disposed at three or more locations. Although the coupling portions 62 do not hinder vibration of the piezoelectric actuator 40, they have effect on the vibration of the piezoelectric actuator 40 to some extent. Because of this, the coupling portions 62 disposed on, for example, three locations can enable the vibrating plate 41 to be supported more naturally, and can also prevent fractures of the piezoelectric element 42.

The piezoelectric element 42 is disposed on the upper surface of the disc-shaped vibrating plate 41. The reinforcement 43 is disposed on the lower surface of the vibrating plate 41. The vibrating plate 41, piezoelectric element 42, and reinforcement 43 constitute the disc-shaped piezoelectric actuator 40. One example of the piezoelectric element 42 may be made of a PZT ceramic material.

The vibrating plate 41 may be made of a metal plate having a coefficient of linear expansion larger than that of each of the piezoelectric element 42 and reinforcement 43, and the metal plate may be solidified by heating at the time of bonding. Thus, warpage of the entire piezoelectric actuator 40 can be avoided, an appropriate compressive stress can remain in the piezoelectric element 42, and fractures of the piezoelectric element 42 can be prevented.

One example of the vibrating plate 41 may be made of a material having a large coefficient of linear expansion, such as phosphor bronze (C5210) or stainless steel SUS301, and one example of the reinforcement 43 may be made of 42 nickel, 36 nickel, or stainless steel SUS430.

The vibrating plate 41, piezoelectric element 42, and reinforcement 43 may be arranged in the order of the piezoelectric element 42, reinforcement 43, and vibrating plate 41 from above. In this case, the coefficients of linear expansion are also adjusted by setting the materials of the reinforcement 43 and vibrating plate 41 such that an appropriate compressive stress remains in the piezoelectric element 42.

The spacer 53B is disposed on the upper surface of the frame plate 61. The spacer 53B is made of a resin. The thickness of the spacer 53B is equal to or slightly larger than that of the piezoelectric element 42. The frame plate 61 electrically insulates the electrode conductive plate 70 and vibrating plate unit 60 from each other.

The electrode conductive plate 70 is disposed on the upper surface of the spacer 53B. The electrode conductive plate 70 is made of a metal. The electrode conductive plate 70 includes a frame member 71 having a substantially circular opening, an inner terminal 73 protruding inside the opening, and an outer terminal 72 protruding out.

The end of the inner terminal 73 is joined to the surface of the piezoelectric element 42 by soldering. By setting the position where they are joined by soldering at the position corresponding to a node of bending vibration of the piezoelectric actuator 40, the vibration of the inner terminal 73 can be suppressed.

The spacer 53C is disposed on the upper surface of the electrode conductive plate 70. The spacer 53C is made of a resin. The spacer 53C has a thickness substantially equal to that of the piezoelectric element 42. The spacer 53C is a spacer for avoiding the solder portion in the inner terminal 73 from coming into contact with the cover plate 54 when the piezoelectric actuator 40 vibrates.

The spacer 53C also prevents a reduction in vibration amplitude caused by air resistance produced by an excessive approach of the surface of the piezoelectric element 42 to the cover plate 54. Because of this, the spacer 53C may have a thickness substantially equal to that of the piezoelectric element 42.

The cover plate 54 is disposed on the upper surface of the spacer 53C. The cover plate 54 has discharge holes 55 and 56. The cover plate 54 covers the upper portion in the piezoelectric actuator 40.

The spacer 53A is disposed on the lower surface of the vibrating plate unit 60. That is, the spacer 53A is disposed between the upper surface of the flexible plate 51 and the lower surface of the vibrating plate unit 60. The thickness of the spacer 53A is the sum of the thickness of the reinforcement 43 and several tens of micrometers. The spacer 53A is a spacer for preventing the piezoelectric actuator 40 from coming into contact with the flexible plate 51 when the piezoelectric actuator 40 vibrates.

The flexible plate 51 is disposed on the lower surface of the spacer 53A. The flexible plate 51 has a suction hole 52 in its center.

The substrate 91 is disposed on the lower surface of the flexible plate 51. The substrate 91 has a substantially cylindrical opening portion 92 in its central portion. The flexible plate 51 includes a fixed portion 57 fixed to the substrate 91 and a movable portion 58. The movable portion 58 is on the central side with respect to the fixed portion 57 and faces the opening portion 92.

The movable portion 58 can be vibrated at a frequency virtually equal to that of the piezoelectric actuator 40 by air pressure fluctuations occurring with vibration of the piezoelectric actuator 40. The natural frequency of the movable portion 58 is designed to be equal to or slightly lower than the driving frequency of the piezoelectric actuator 40.

When the vibration phase of the flexible plate 51 is designed to lag behind the vibration phase of the piezoelectric actuator 40 (for example, lag by 90 degrees), the variations in thickness of the gap between the flexible plate 51 and piezoelectric actuator 40 virtually increases.

Accordingly, when an alternating driving voltage is applied to the outer terminals 63 and 72, the piezoelectric actuator 40 concentrically bends and vibrates. The movable portion 58 in the flexible plate 51 also vibrates with the vibration of the piezoelectric actuator 40.

Thus, the piezoelectric pump 10 sucks air through the opening portion 92 and suction hole 52 into the pump chamber 45. The piezoelectric pump 10 discharges the air from the pump chamber 45 through the discharge holes 55 and 56.

At this time, the peripheral portion in the piezoelectric actuator 40 in the piezoelectric pump 10 is not virtually fixed. Because of this, the piezoelectric pump 10 can provide a high discharge pressure and a large discharge flow rate with a small loss during vibration of the piezoelectric actuator 40 and with a reduced size and low profile.

Next, the structure of the valve 101 is described with reference to FIGS. 1, 3, and 4.

Figure 3:
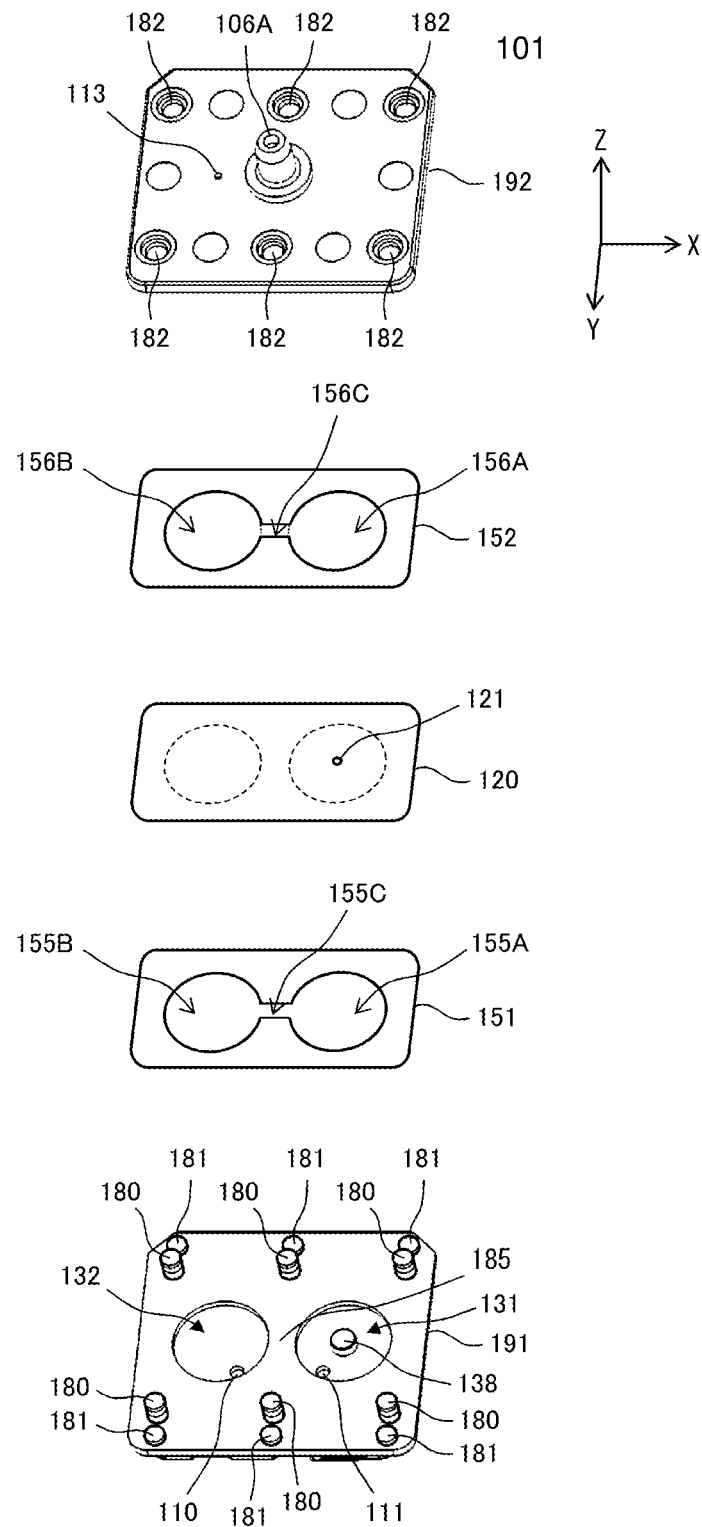
FIG. 3 is an exploded perspective view of a valve 101 illustrated in FIG. 1.
Figure 4:
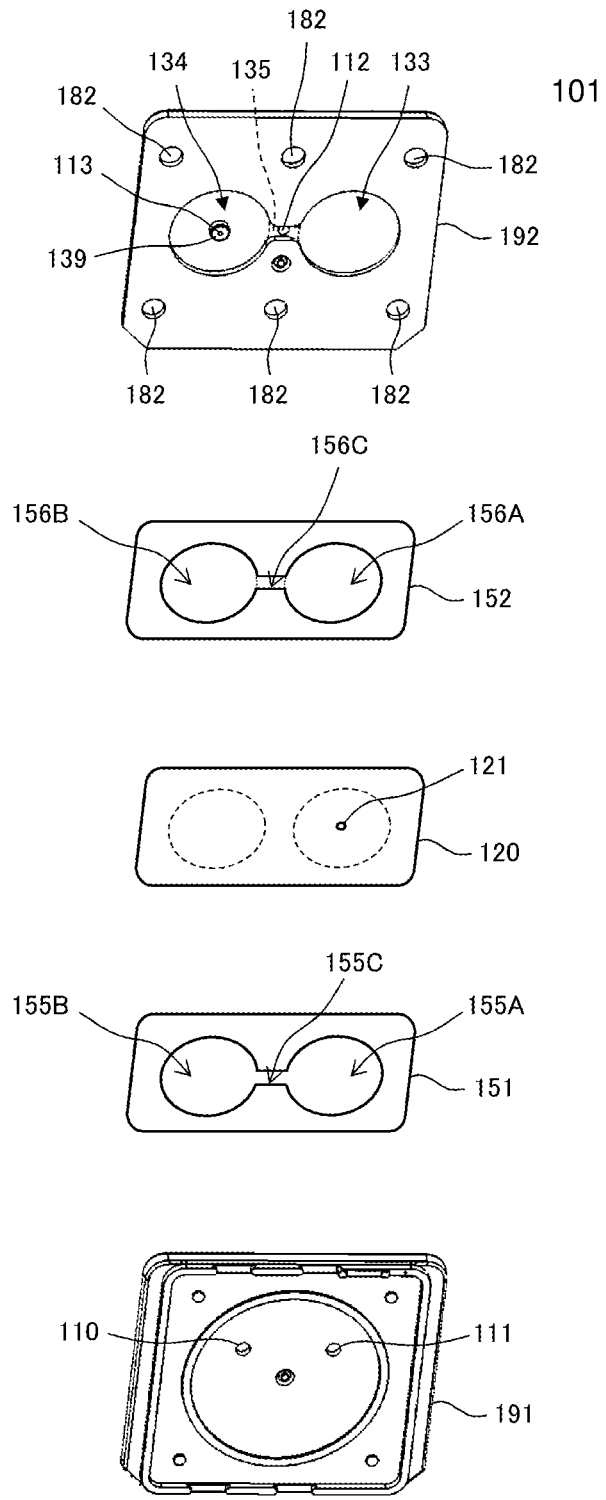
FIG. 4 is an exploded perspective view of the valve 101 illustrated in FIG. 1.

FIGS. 3 and 4 are exploded perspective views that illustrate the valve 101 illustrated in FIG. 1. FIG. 3 is an exploded perspective view of the valve 101 seen from the upper surface side connected to the cuff 109. FIG. 4 is an exploded perspective view of the valve 101 seen from the bottom surface side joined to the piezoelectric pump 10.

A z-axis direction, y-axis direction, and x-axis direction are illustrated in FIG. 3. The z-axis direction indicates a direction in which the members constituting the valve 101 are laminated. The x-axis direction indicates a direction in which a check valve 160, the communication path 135, and an exhaust valve 170 are arranged. The y-axis direction indicates a direction perpendicular to the z-axis direction and x-axis direction.

One example of a "first valve chamber" in the present disclosure corresponds to a lower valve chamber 131 and a lower valve chamber 132. One example of a "second valve chamber" in the present disclosure corresponds to an upper valve chamber 133 and an upper valve chamber 134. One example of a "first valve seat" in the present disclosure corresponds to a valve seat 138. One example of a "second valve seat" in the present disclosure corresponds to a valve seat 139.

As illustrated in FIGS. 1, 3, and 4, the valve 101 includes a first valve housing 191, a second seal member 152 made of a substantially rectangular thin film, a diaphragm 120 made of a substantially rectangular thin film, a first seal member 151 made of a substantially rectangular thin film, and a second valve housing 192 and has a structure in which they are laminated in sequence.

As illustrated in FIGS. 1, 3, and 4, the second valve housing 192 has a second vent hole 112 communicating with the inner space of the cuff 109, a third vent hole 113 communicating with the outside of the sphygmomanometer device 100, and the valve seat 139 protruding from the periphery of the third vent hole 113 toward the diaphragm 120 and six opening portions 182. One example of the second valve housing 192 may be made of a resin. The valve seat 139 has a substantially cylindrical shape having the third vent hole 113 in its central portion.

The six opening portions 182 in the second valve housing 192 are nearer the outer edge side than the lower valve chamber 131 and lower valve chamber 132, which are described below, as seen in plan view from the z-axis direction. Of the six opening portions 182, three opening portions 182 are arranged along the x-axis direction.

The other three opening portions 182 are arranged along the x-axis direction such that they are aligned in parallel to the above-described three opening portions 182 on the side opposite to the side where the above-described three opening portions 182 are positioned and such that the lower valve chamber 131 and lower valve chamber 132 are disposed therebetween.

As illustrated in FIG. 1, the upper surface of the piezoelectric pump 10 is bonded to the bottom surface of the first valve housing 191. As illustrated in FIGS. 1, 3, and 4, the first valve housing 191 has a first vent hole 110 communicating with the discharge hole 56 in the piezoelectric pump 10, a first vent hole 111 communicating with the discharge hole 55 in the piezoelectric pump 10, and a valve seat 138 protruding toward the diaphragm 120 and six first protruding portions 180 opposed to the six opening portions 182.

One example of the first valve housing 191 may be made of a resin. The valve seat 138 has a substantially columnar shape. The six opening portions 180 in the first valve housing 191 are nearer the outer edge side than the upper valve chamber 133 and upper valve chamber 134, which are described below, as seen in plan view from the z-axis direction.

The first valve housing 191 further includes six second protruding portions 181 nearer the outer edge side than the six first protruding portions 180, as seen in plan view from the z-axis direction.

The six second protruding portions 181 are nearer the outer edge side than the second seal member 152, diaphragm 120, and first seal member 151, as seen in plan view from the z-axis direction, in the state where the six first protruding portions 180 are engaged in the six opening portions 182.

As illustrated in FIGS. 1, 3, and 4, the diaphragm 120 has a circular opening portion 121 in a central portion in an area opposed to the valve seat 138. The diameter of the opening portion 121 is smaller than that of the surface of the valve seat 138 in contact with the diaphragm 120.

The perimeter of the diaphragm 120 is smaller than that of each of the second valve housing 192 and first valve housing 191. One example of the diaphragm 120 may be made of a rubber, such as ethylene propylene diene monomer (EPDM) rubber or silicone.

The diaphragm 120 is held between the second valve housing 192 and first valve housing 191 with the second seal member 152 and first seal member 151 interposed therebetween by engagement of the six first protruding portions 180 with the six opening portions 182.

That is, the diaphragm 120 is fixed to the second valve housing 192 and first valve housing 191 such that it is separated from the valve seat 139 and the periphery of the opening portion 121 in the diaphragm 120 is in contact with the valve seat 138 while providing a pressure thereto.

Thus, the diaphragm 120 covers an area inside the six opening portions 182 in the second valve housing 192, as seen in plan view from the z-axis direction, and an area inside the six first protruding portions 180 in the first valve housing 191, as seen in plan view from the z-axis direction.

The diaphragm 120 divides the inside of the second valve housing 192 and first valve housing 191. Thus, the diaphragm 120 defines the annular lower valve chamber 131 communicating with the first vent hole 111 and the columnar upper valve chamber 133 communicating with the second vent hole 112 with the communication path 135 interposed therebetween, together with the second valve housing 192 and first valve housing 191.

The diaphragm 120 defines the columnar lower valve chamber 132 communicating with the first vent hole 110 and the annular upper valve chamber 134 communicating with the upper valve chamber 133 with the communication path 135 interposed therebetween, together with the second valve housing 192 and first valve housing 191.

The diaphragm 120 defines the check valve 160, together with the second valve housing 192 and first valve housing 191. The diaphragm 120 defines the exhaust valve 170, together with the second valve housing 192 and first valve housing 191.

The check valve 160, communication path 135, and exhaust valve 170 are arranged along the x-axis direction.

The second seal member 152 has second through holes 156A to 156C in an area that faces the upper valve chamber 133, communication path 135, and upper valve chamber 134. One example of the second through hole 156A may have a substantially circular shape whose central axis is approximately the same as that of the upper valve chamber 133. One example of the second through hole 156B may have a substantially circular shape whose central axis is approximately the same as that of the upper valve chamber 134.

One example of each of the second through holes 156A and 156B may have a diameter of 6.6 mm. That is, the perimeter of the second seal member 152 is smaller than that of each of the second valve housing 192 and first valve housing 191. One example of the second seal member 152 may be made of double-sided tape or an adhesive.

The first seal member 151 has first through holes 155A to 155C in an area that faces the lower valve chamber 131 and lower valve chamber 132. One example of the first through hole 155A may have a substantially circular shape whose central axis is approximately the same as that of the lower valve chamber 131. One example of the first through hole 155B may have a substantially circular shape whose central axis is approximately the same as that of the lower valve chamber 132.

One example of each of the first through holes 155A and 155B may have a diameter of 6.6 mm. That is, the perimeter of the first seal member 151 is smaller than that of each of the second valve housing 192 and first valve housing 191. One example of the first seal member 151 may be made of double-sided tape or an adhesive.

The diameter of the first through hole 155A is larger than that of the valve seat 138 and smaller than that of the lower valve chamber 131. That is, the perimeter of the first through hole 155A is larger than that of the valve seat 138 and smaller than that of the lower valve chamber 131.

Similarly, the diameter of the first through hole 155B is smaller than that of the lower valve chamber 132. That is, the perimeter of the first through hole 155B is smaller than that of the lower valve chamber 132.

In the valve 101, part of the second seal member 152 is positioned in the upper valve chamber 133 and upper valve chamber 134. Similarly, part of the first seal member 151 is positioned in the lower valve chamber 131 and lower valve chamber 132.

The check valve 160 is constituted of part of the first valve housing 191 having the first vent hole 111, part of the second valve housing 192 having the second vent hole 112, the periphery of the opening portion 121 in the diaphragm 120, and the valve seat 138 protruding toward the diaphragm 120. The check valve 160 permits a fluid flow from the lower valve chamber 131 toward the upper valve chamber 133 and interrupts a fluid flow from the upper valve chamber 133 toward the lower valve chamber 131.

In the check valve 160, the periphery of the opening portion 121 in the diaphragm 120 is in contact with or is separated from the valve seat 138, depending on the pressure provided by contact of the periphery of the opening portion 121 in the diaphragm 120 with the valve seat 138, the pressure from the lower valve chamber 131, and the pressure from the upper valve chamber 133.

The exhaust valve 170 is constituted of part of the first valve housing 191 having the first vent hole 110, part of the second valve housing 192 having the second vent hole 112 and third vent hole 113, part of the diaphragm 120, and the valve seat 139 protruding from the periphery of the third vent hole 113 toward the diaphragm 120.

In the exhaust valve 170, part of the diaphragm 120 is in contact with or is separated from the valve seat 139, depending on the pressure difference between the lower valve chamber 132 and upper valve chamber 134.

As illustrated in FIGS. 3 and 4, in the valve 101, because each of the valve chambers 131, 132, 133, and 134 has a substantially circular external shape, uniform tension is applied to the diaphragm 120 (in particular the periphery in the vicinity of the opening portion 121).

Because of this, contact in the state where the opening portion 121 in the diaphragm 120 is inclined with respect to the valve seats 138 and 139 or displacement of the opening portion 121 in the diaphragm 120 in a horizontal direction with respect to the valve seats 138 and 139 are suppressed. Accordingly, the valve 101 can enable each valve to be reliably opened or closed.

As illustrated in FIG. 1, the relationship $w=3/16 \times ((1-v^2)/(E \times t^3)) \times P \times (r^2-a^2)^2$ is satisfied, where E denotes the Young's modulus of the diaphragm 120, v denotes the Poisson's ratio of the diaphragm 120, a denotes the radius of the portion receiving a pressure in the lower valve chamber 132 in the diaphragm 120, t denotes the thickness of the diaphragm 120, r denotes the distance from the central axis C of the diaphragm 120 to the outermost peripheral point in the perimeter of the third vent hole 113, and w denotes the swelling amount at a location S on the above-described peripheral point axis in the diaphragm 120 when the pressure difference P is applied (reference: Inoue Tatsuo, Dansei Rikigaku No Kiso (Fundamentals of Elastodynamics), Nikkan Kogyo Shimbun Ltd., March 1979).

At this time, the valve 101 satisfies the relationship $y<3/16 \times ((1-v^2)/(E \times t^3)) \times P3 \times (r^2-a^2)^2$, where P3 denotes the provided pressure and y denotes the distance from the location S on the above-described peripheral point axis in the diaphragm 120 to the valve seat 139.

The third vent hole 113 is fully closed by the diaphragm 120 by contact of the point S in the diaphragm 120 with the valve seat 139.

As illustrated in FIG. 1, in the valve 101, the length A in which the valve seat 138 depresses the diaphragm 120 is shorter than the length y from the location S on the above-described peripheral point axis in the diaphragm 120 to the valve seat 139. Thus, the valve 101 satisfies the relationship $y<3/16 \times ((1-v^2)/(E \times t^3)) \times P3 \times (r^2-a^2)^2$.

Figure 6:
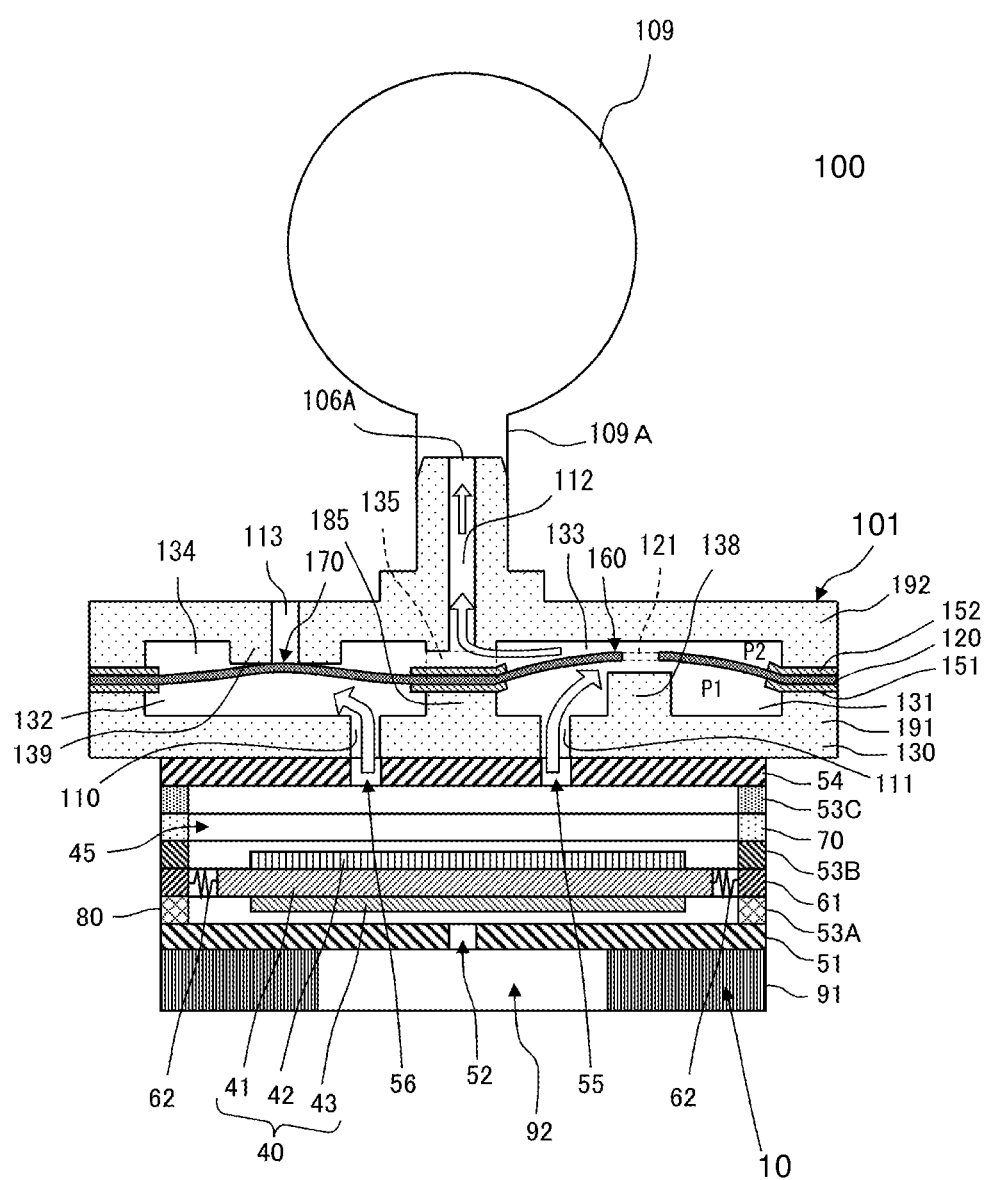
FIG. 6 is an explanatory drawing that illustrates an air stream in the sphygmomanometer device 100 while the piezoelectric pump 10 illustrated in FIG. 1 is driven.
Figure 7:
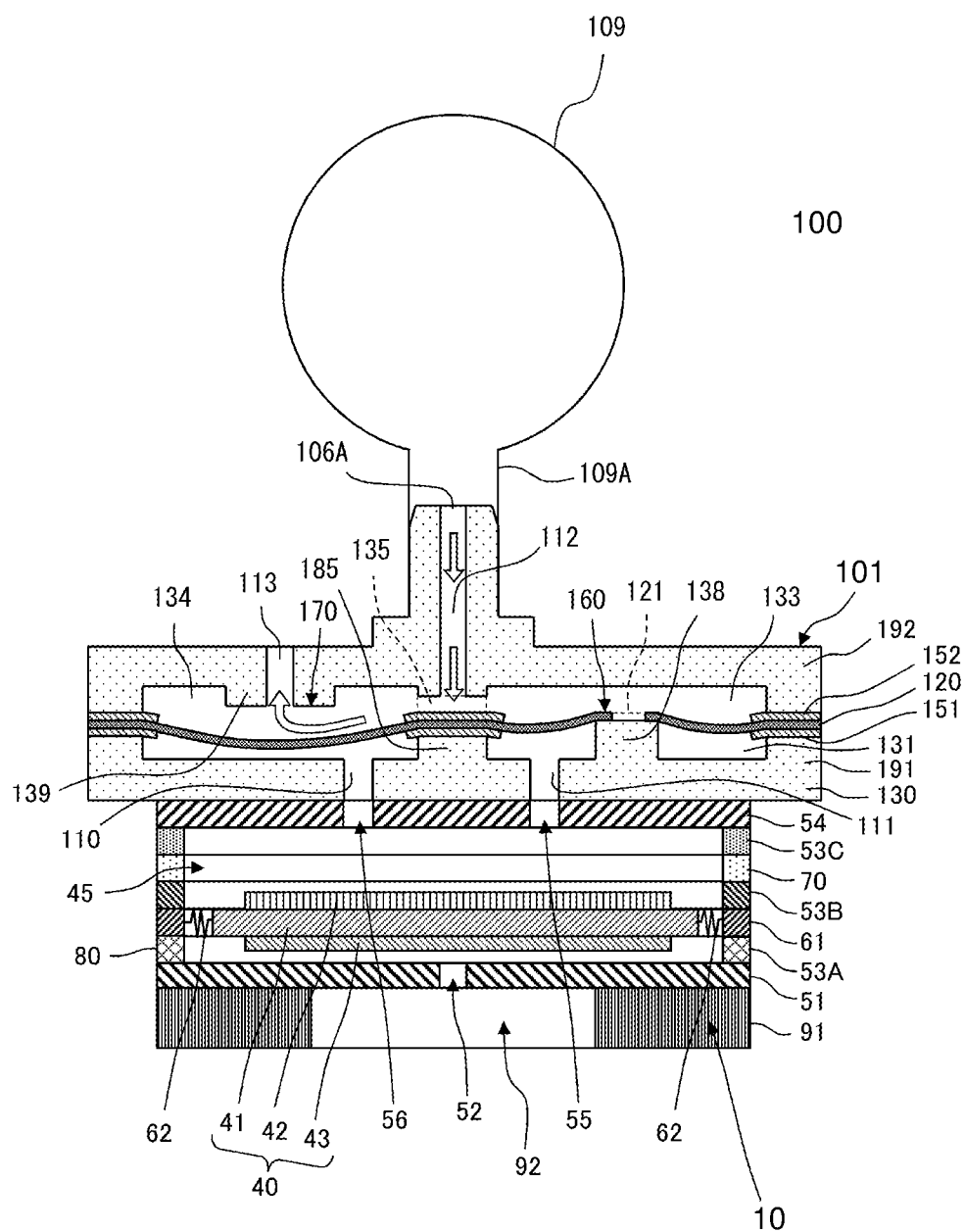
FIG. 7 is an explanatory drawing that illustrates an air stream in the sphygmomanometer device 100 immediately after the piezoelectric pump 10 illustrated in FIG. 1 is deactivated.
Figure 8:
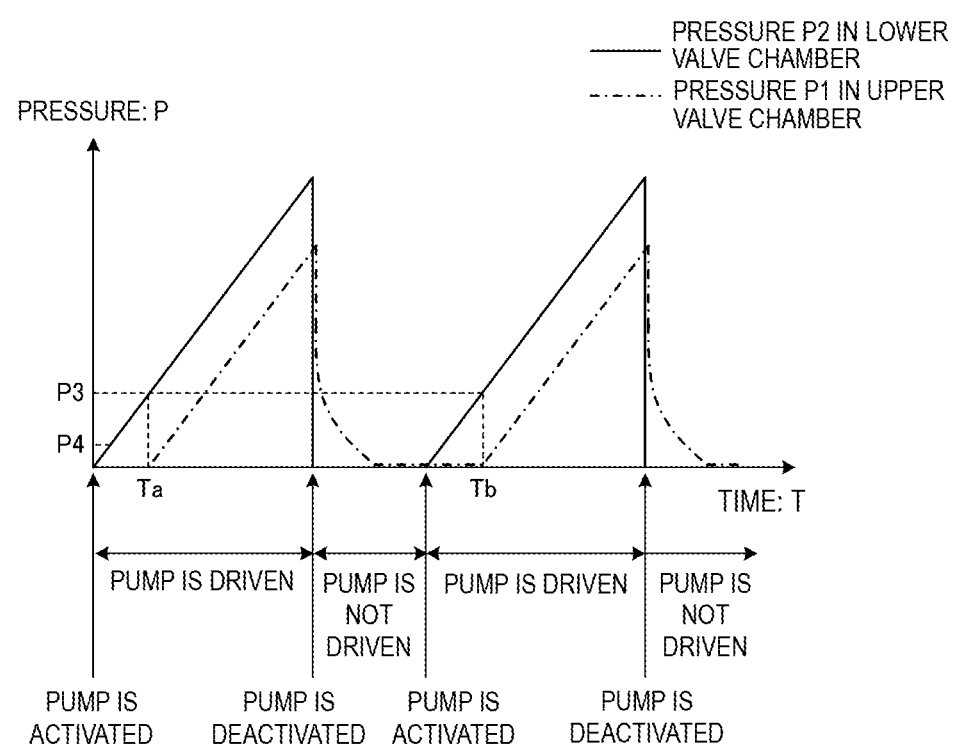
FIG. 8 illustrates pressure changes in an upper valve chamber 134 included in the valve 101 illustrated in FIG. 1 and pressure changes in a lower valve chamber 132.

Because of this, the valve 101 can achieve air streams illustrated in FIGS. 1 and 5 to 7 and pressure changes illustrated in FIG. 8 in blood pressure measurement.

Figure 5:
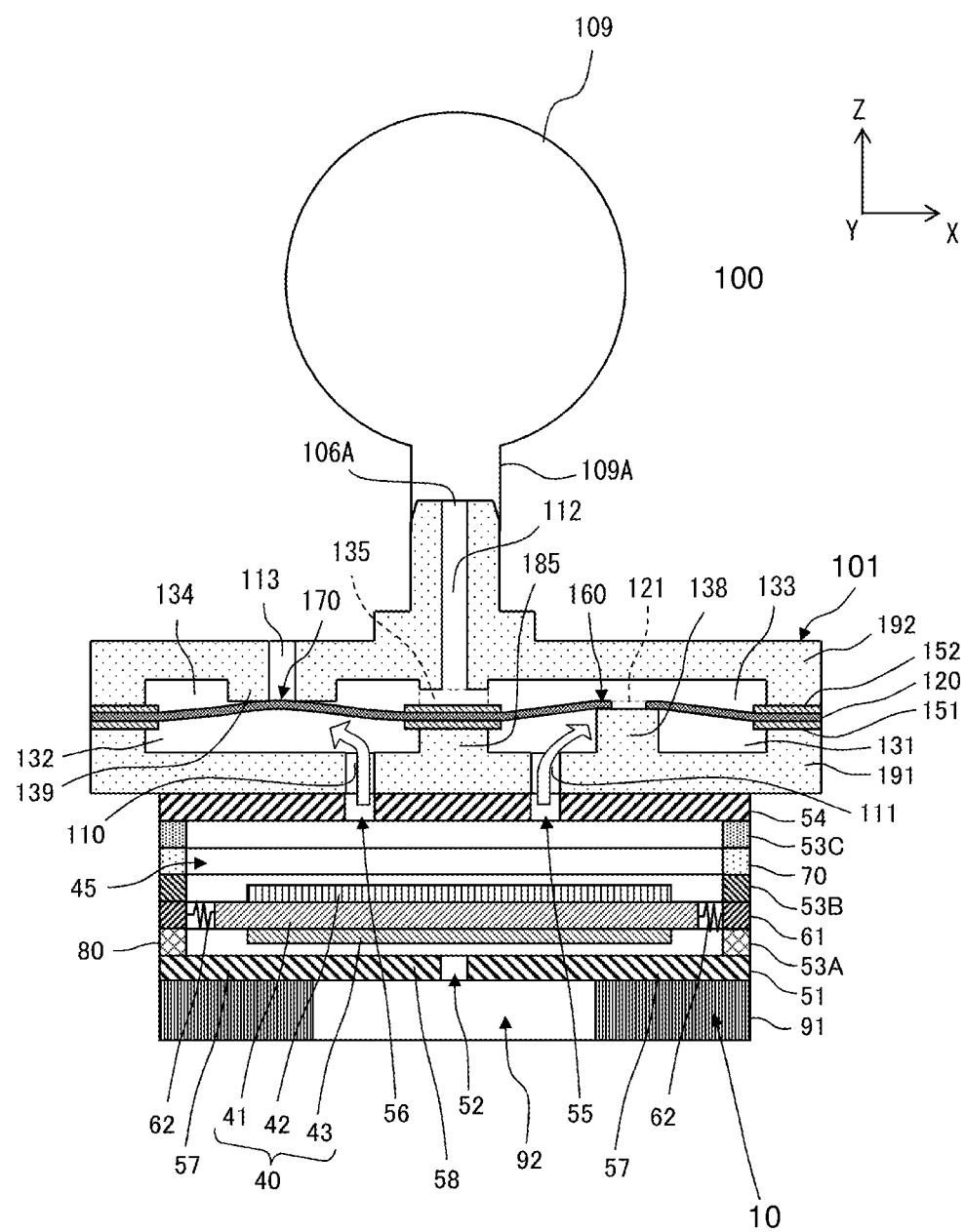
FIG. 5 is an explanatory drawing that illustrates an air stream in the sphygmomanometer device 100 immediately after the piezoelectric pump 10 illustrated in FIG. 1 is activated.

FIG. 5 is an explanatory drawing that illustrates an air stream in the sphygmomanometer device 100 immediately after the piezoelectric pump 10 illustrated in FIG. 1 is activated. FIG. 6 is an explanatory drawing that illustrates an air stream in the sphygmomanometer device 100 while the piezoelectric pump 10 illustrated in FIG. 1 is driven. FIG. 7 is an explanatory drawing that illustrates an air stream in the sphygmomanometer device 100 immediately after the piezoelectric pump 10 illustrated in FIG. 1 is deactivated. FIG. 8 illustrates pressure changes in the upper valve chamber 134 included in the valve 101 illustrated in FIG. 1 and pressure changes in the lower valve chamber 132.

FIG. 8 illustrates behavior in two blood pressure measurements in graph form. In FIG. 8, Ta indicates the amount of time elapsed from the first-time activation of the piezoelectric pump 10 to the state where the pressure P2 in the lower valve chamber 132 becomes equal to or higher than the provided pressure P3 (that is, to the state where the check valve 160 is opened). In FIG. 8, Tb indicates the amount of time elapsed from the second-time activation of the piezoelectric pump 10 to the state where the pressure P2 in the lower valve chamber 132 becomes equal to or higher than the provided pressure P3 (that is, to the state where the check valve 160 is opened).

First, the air stream in the sphygmomanometer device 100 immediately after the piezoelectric pump 10 is activated is described with reference to FIGS. 5 and 8.

The sphygmomanometer device 100 activates the piezoelectric pump 10 to start a blood pressure measurement. When the piezoelectric pump 10 is activated, first, air flows into the pump chamber 45 inside the piezoelectric pump 10 through the opening portion 92 and suction hole 52. Next, the air is discharged through the discharge holes 55 and 56 and flows into both the lower valve chamber 132 and lower valve chamber 131 in the valve 101.

Thus, in the exhaust valve 170, when the pressure P2 in the lower valve chamber 132 is higher than the pressure P1 in the upper valve chamber 134 and lower than the provided pressure P3 (specifically, when the pressure P2 in the lower valve chamber 132 is equal to or higher than the valve closing pressure P4 and lower than the provided pressure P3 in FIG. 8), the diaphragm 120 is in contact with the valve seat 139, as illustrated in FIG. 5.

Thus, in the exhaust valve 170, the diaphragm 120 closes the third vent hole 113, and the second vent hole 112 and third vent hole 113 lose communication. That is, the exhaust valve 170 is closed.

Next, the air stream in the sphygmomanometer device 100 while the piezoelectric pump 10 is driven is described with reference to FIGS. 6 and 8.

When the pressure P2 in the lower valve chamber 132 is equal to or higher than the provided pressure P3 after the exhaust valve 170 is closed (see FIG. 8), in the check valve 160, the periphery of the opening portion 121 in the diaphragm 120 is separated from the valve seat 138, as illustrated in FIG. 6. Thus, the first vent hole 111 and second vent hole 112 start communication with each other with the opening portion 121 interposed therebetween. That is, the check valve 160 is opened.

Consequently, air is sent from the piezoelectric pump 10 through the first vent hole 111, opening portion 121, and second vent hole 112 in the valve 101 to the cuff 109 (see FIG. 6), and the pressure (air pressure) inside the cuff 109 is increased.

The diaphragm 120 is fixed to the second valve housing 192 and first valve housing 191 such that the periphery of the opening portion 121 in the diaphragm 120 is in contact with the valve seat 138. This valve seat 138 provides a pressure to the periphery of the opening portion 121 in the diaphragm 120.

Thus, the air flowing through the first vent hole 111 in the valve 101 out of the opening portion 121 flows into the upper valve chamber 133 and upper valve chamber 134 through the opening portion 121 with a pressure slightly lower than the discharge pressure of the piezoelectric pump 10. The discharge pressure of the piezoelectric pump 10 is applied to the lower valve chamber 132.

Consequently, in the valve 101, as illustrated in FIG. 8, the pressure P2 in the lower valve chamber 132 is a little higher than the pressure P1 in the upper valve chamber 134, and the state in which the diaphragm 120 seals the third vent hole 113 and the opening portion 121 is open is maintained.

Next, the air stream in the sphygmomanometer device 100 immediately after the piezoelectric pump 10 is deactivated is described with reference to FIGS. 7 and 8.

When the blood pressure measurement ends, the sphygmomanometer device 100 deactivates the piezoelectric pump 10. When the piezoelectric pump 10 is deactivated, the air in the pump chamber 45, lower valve chamber 131, and lower valve chamber 132 is quickly exhausted to the outside of the sphygmomanometer device 100 through the suction hole 52 and opening portion 92 in the piezoelectric pump 10. The pressure in the cuff 109 is applied to the upper valve chamber 133 and upper valve chamber 134 through the second vent hole 112.

Consequently, in the check valve 160, the pressure P2 in the lower valve chamber 132 becomes lower than the pressure P1 in the upper valve chamber 134. Thus, the diaphragm 120 comes into contact with the valve seat 138, and the opening portion 121 is sealed.

In the exhaust valve 170, the pressure P2 in the lower valve chamber 132 becomes lower than the pressure P1 in the upper valve chamber 134. Thus, the diaphragm 120 becomes separated from the valve seat 139 and opens the third vent hole 113.

That is, in the valve 101, the second vent hole 112 and third vent hole 113 start communication with each other with the communication path 135 and upper valve chamber 134 interposed therebetween. Thus, the air in the cuff 109 is quickly exhausted from the third vent hole 113 through the second vent hole 112, communication path 135, and upper valve chamber 134 (see FIG. 7). Thus, because the cuff 109 quickly shrinks, the sphygmomanometer device 100 becomes ready to start a next blood pressure measurement at once.

At this time, in the valve 101, because the diaphragm 120 is fixed to the second valve housing 192 and first valve housing 191 such that it is separated from the valve seat 139, the diaphragm 120 does not close the third vent hole 113. That is, the valve 101 is maintained in the state where the second vent hole 112 and third vent hole 113 communicate with each other.

Because of this, in the valve 101, the air inside the cuff 109 is fully exhausted until the pressure inside the cuff 109 reaches atmospheric pressure. Hence, unlike the valve 901 in Patent Document 1, the valve 101 has no error corresponding to the amount of pressure remaining in the cuff 109.

Accordingly, the valve 101 can enable the cuff 109 to be filled with compressed air and can enable the air to be exhausted from the cuff 109 until the pressure in the cuff 109 reaches atmospheric pressure.

At the exhaust time, in which the diaphragm 120 is separated from the valve seat 139, vibration of the diaphragm 120 produces an exhaust sound. As the valve opening pressure for the valve seat 139 increases (that is, the tension of the diaphragm 120 increases), the vibration of the diaphragm 120 increases and the exhaust sound increases.

The valve opening pressure for the valve seat 139 in the valve 101 having the above-described configuration is zero. Because of this, the valve 101 having the above-described configuration can suppress an exhaust sound during the exhaust.

As previously described, in the valve 101, part of the first seal member 151 is positioned inside the lower valve chamber 131 and lower valve chamber 132, and part of the second seal member 152 is positioned inside the upper valve chamber 133 and upper valve chamber 134.

Because of this, the second seal member 152 and first seal member 151 can bond the second valve housing 192, first valve housing 191, and diaphragm 120 together and can capture foreign matter present inside each of the valve chambers 131, 132, 133, and 134.

Accordingly, if foreign matter enters the valve 101, it can suppress malfunctions caused by foreign matter. In particular, in the exhaust valve 170, closure of the third vent hole 113 in the valve seat 139 with foreign matter can be suppressed.

The sphygmomanometer device 100 including the valve 101 according to the present embodiment can also offer substantially the same advantages.

Figure 17:
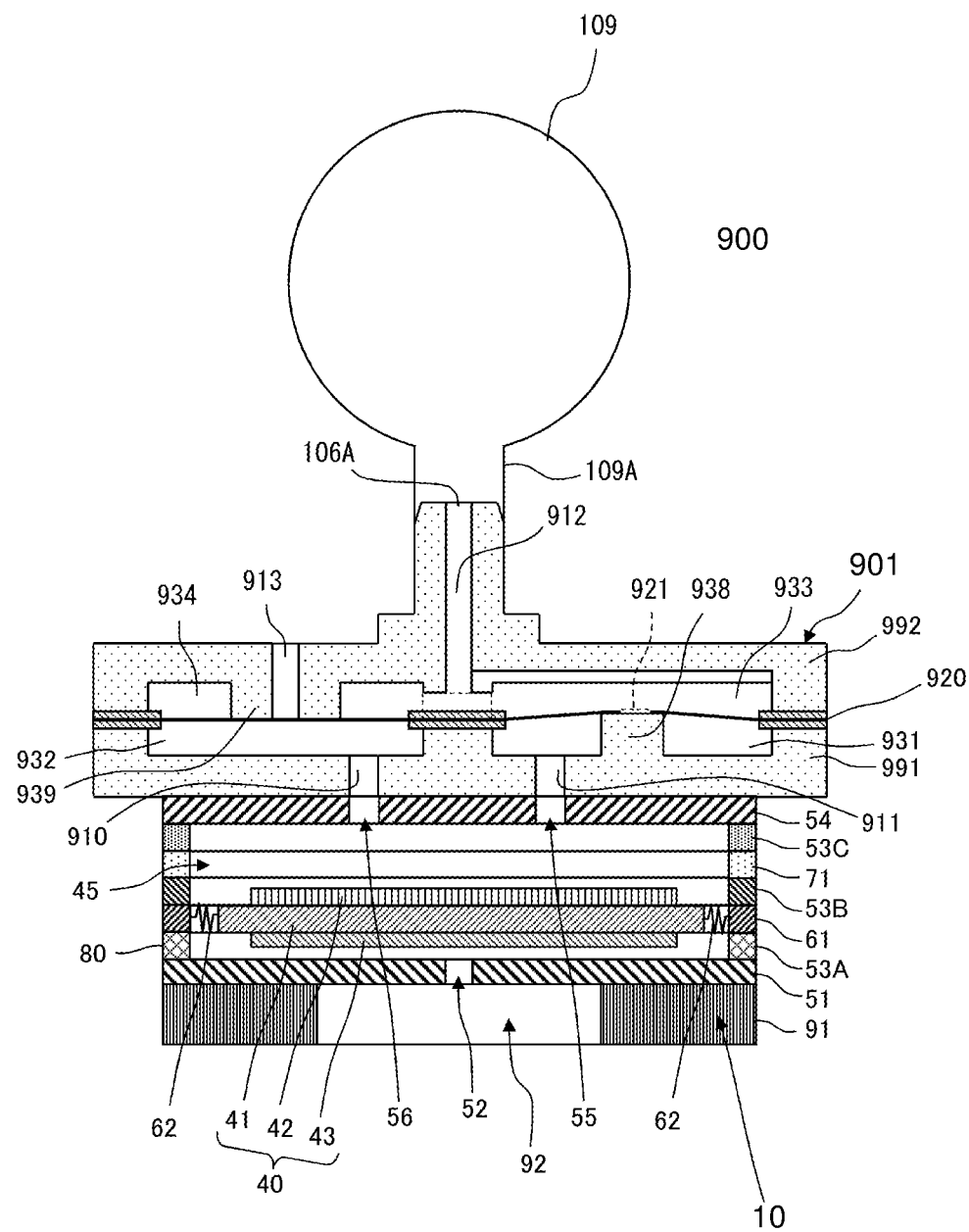
FIG. 17 is a cross-sectional view of a main portion in a fluid control device 900 according to Patent Document 1.
Figure 18:
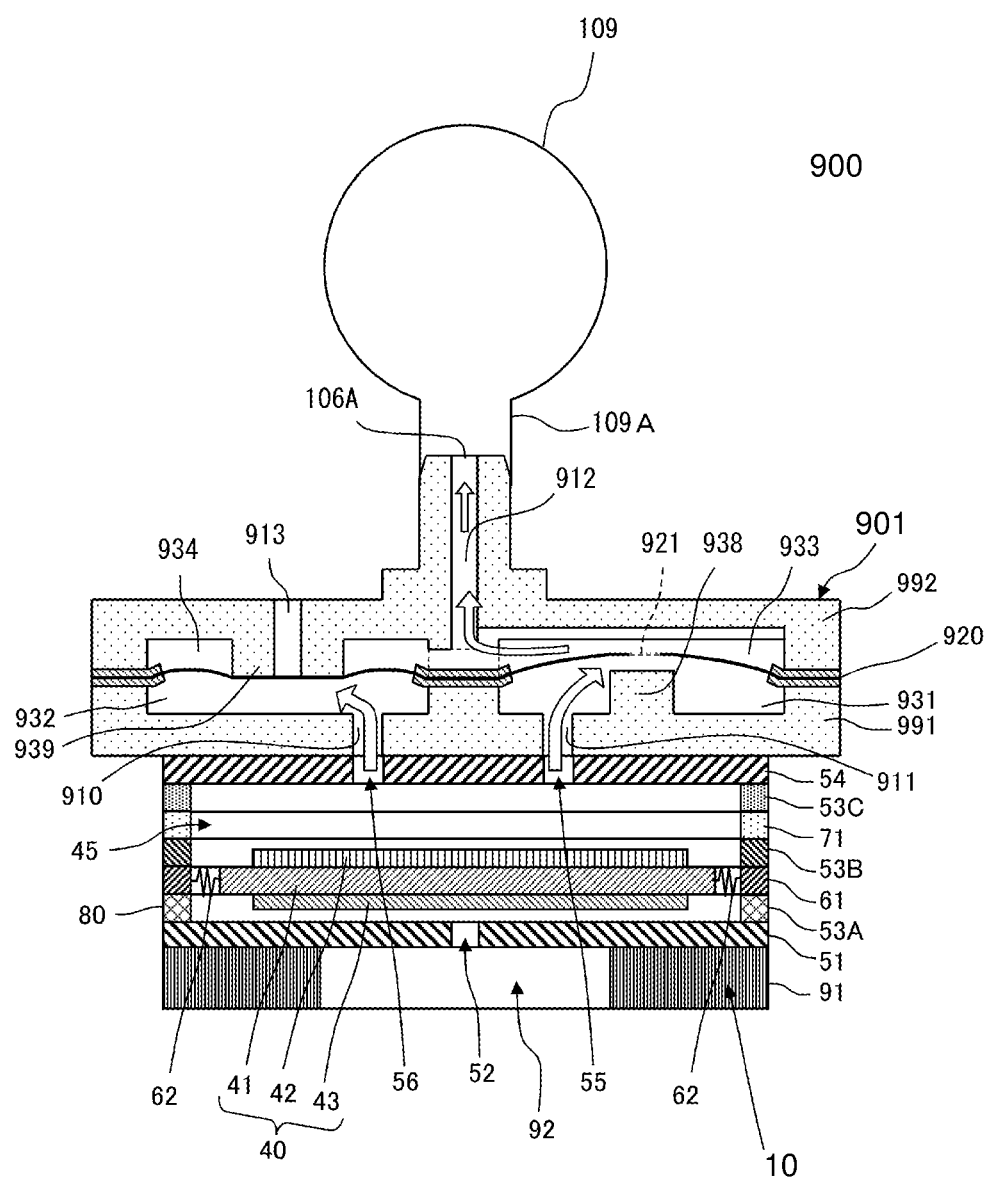
FIG. 18 is an explanatory drawing that illustrates an air stream in the fluid control device 900 while the piezoelectric pump 10 illustrated in FIG. 17 is driven.
Figure 19:
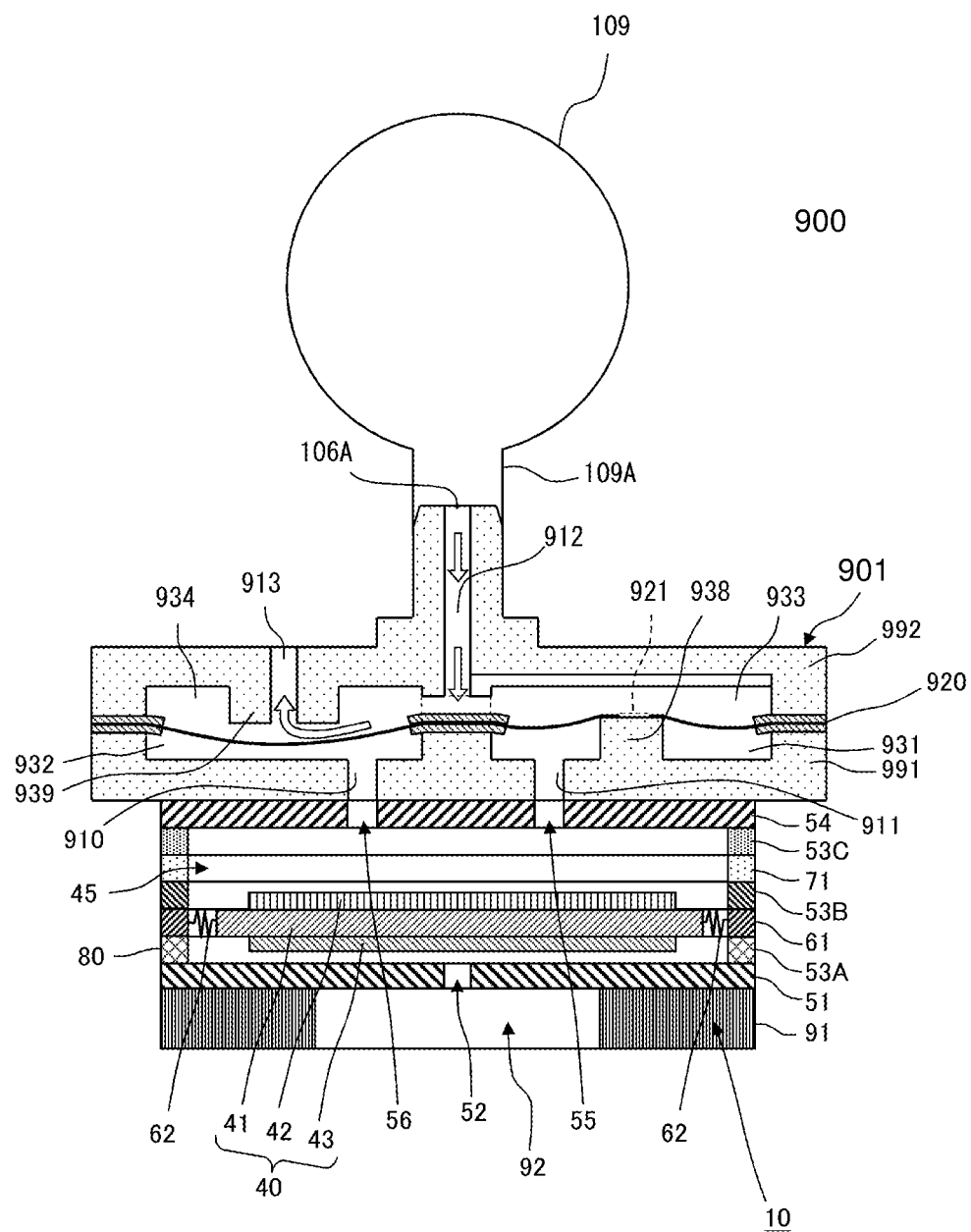
FIG. 19 is an explanatory drawing that illustrates an air stream in the fluid control device 900 immediately after the piezoelectric pump 10 illustrated in FIG. 17 is deactivated.
Figure 20:
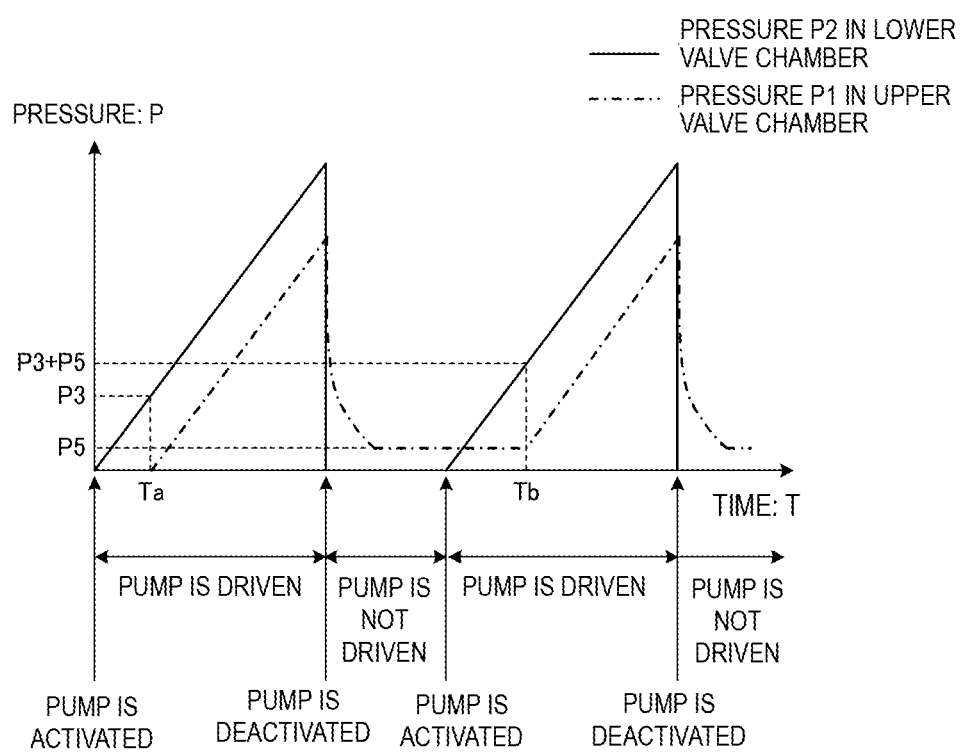
FIG. 20 illustrates pressure changes in the upper valve chamber 934 included in the valve 901 illustrated in FIG. 17 and pressure changes in a lower valve chamber 932.

Below is comparison between the valve 101 according to the first embodiment of the present disclosure (see FIG. 1) and the valve 901 according to Patent Document 1 (see FIG. 17).

One of the main points of difference between the valve 101 and valve 901 is that the diaphragm 120 in the valve 101 is fixed to the second valve housing 192 and first valve housing 191 such that the diaphragm 120 is separated from the valve seat 139 and the periphery of the opening portion 121 in the diaphragm 120 is in contact with the valve seat 138 while providing a pressure thereto.

Specifically, the valve 101 differs from the valve 901 in that the valve 101 satisfies the relationship $y<3/16\times((1-v^2)/(E\times t^3))\times P3\times(r^2-a^2)^2$, as previously described.

Figure 9:
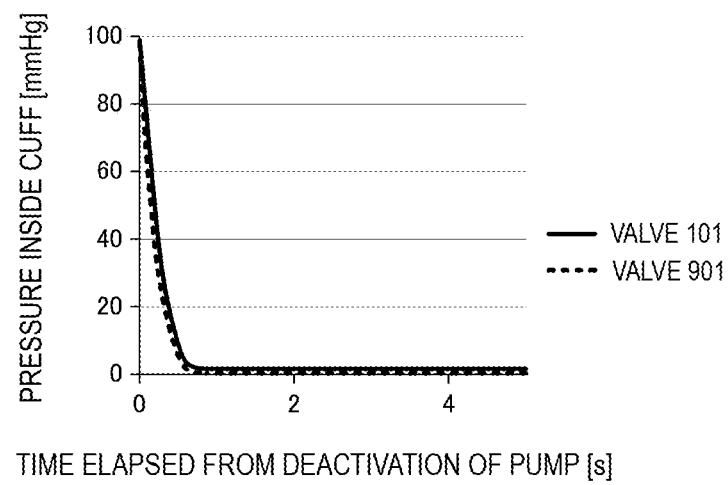
FIG. 9 illustrates pressure changes in the upper valve chamber 134 included in the valve 101 immediately after the piezoelectric pump 10 illustrated in FIG. 1 is deactivated and pressure changes in an upper valve chamber 934 in a valve 901 according to Patent Document 1.
Figure 10:
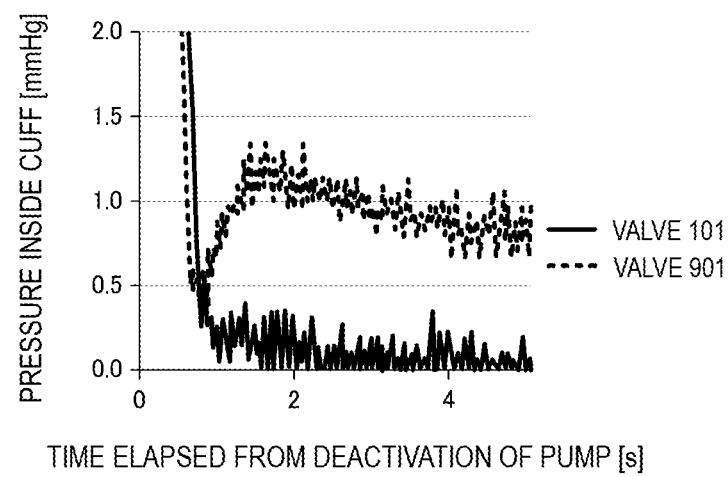
FIG. 10 is an enlarged view of part of a graph illustrated in FIG. 9.

FIG. 9 illustrates pressure changes in the upper valve chamber 134 included in the valve 101 illustrated in FIG. 1 immediately after the piezoelectric pump 10 illustrated in FIG. 1 is deactivated and pressure changes in the upper valve chamber 934 in the valve 901 according to Patent Document 1. FIG. 10 is an enlarged view of part of the graph illustrated in FIG. 9.

FIGS. 9 and 10 illustrate experimental results of measurement of pressure changes in the upper valve chamber 134 in the valve 101 and pressure changes in the upper valve chamber 934 in the valve 901 according to Patent Document 1 immediately after the cuff 109 with a capacity of 50 cc is filled with compressed air up to 100 mmHg and then the piezoelectric pump 10 is deactivated.

The experiment reveals that in the case of the valve 901 the pressure inside the cuff 109 remains higher than atmospheric pressure, whereas in the case of the valve 101 the air inside the cuff 109 is fully exhausted until the pressure inside the cuff 109 reaches atmospheric pressure, as illustrated in FIG. 10.

The conceivable reason for that result is described below. In the case of the valve 901, before the pressure inside the cuff 109 becomes equal to atmospheric pressure, the diaphragm 920 closes the third vent hole 913 in the valve seat 939.

In contrast, in the case of the valve 101, the diaphragm 120 is fixed to the second valve housing 192 and first valve housing 191 such that it is separated from the valve seat 139. That is, the reason may be that in the case of the valve 101, the diaphragm 120 does not close the third vent hole 113, and the state where the second vent hole 112 and third vent hole 113 communicate with each other is maintained.

Accordingly, in the case of the valve 101 according to the present embodiment, the cuff 109 can be filled with compressed air, and the air inside the cuff 109 can be exhausted until the pressure inside the cuff 109 reaches atmospheric pressure.

A sphygmomanometer device 200 according to a second embodiment of the present disclosure is described below.

Figure 11:
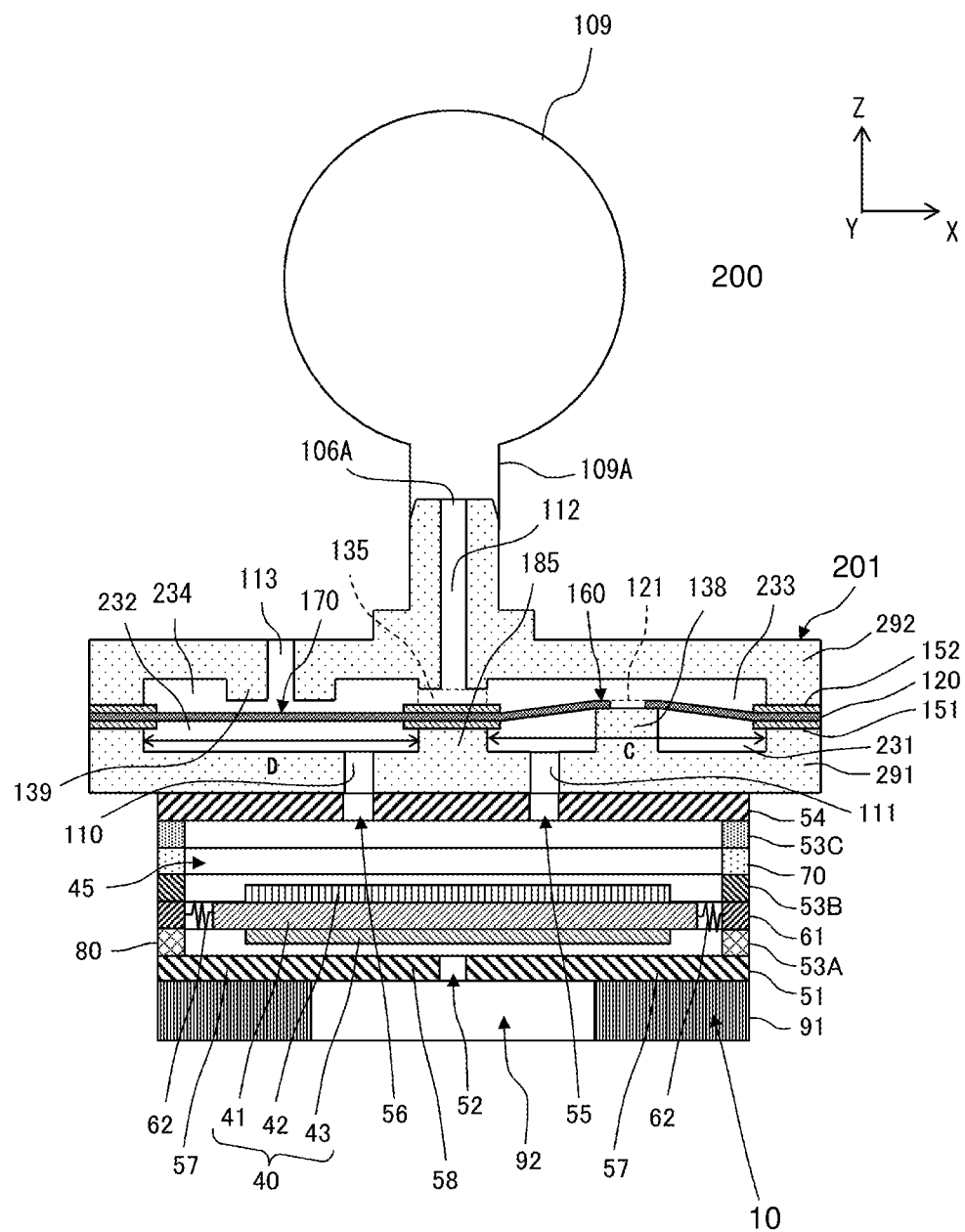
FIG. 11 is a cross-sectional view of a main portion in a sphygmomanometer device 200 according to a second embodiment of the present disclosure.

FIG. 11 is a cross-sectional view of a main portion in the sphygmomanometer device 200 according to the second embodiment of the present disclosure.

The sphygmomanometer device 200 differs from the sphygmomanometer device 100 in a second valve housing 292 and a first valve housing 291 included in a valve 201. The other configurations are the same, and the description thereof is omitted.

In the valve 201, the diameter D of a upper valve chamber 234 is larger than the diameter C of an upper valve chamber 233, and the diameter D of a lower valve chamber 232 is larger than the diameter C of a lower valve chamber 231. Because of this, in the valve 201, a location on the central axis of the third vent hole 113 in the diaphragm 120 is displaced more largely than the center of the opening portion 121.

With this structure, the valve 201 satisfies the relationship $y<3/16\times((1-v^2)/(E\times t^3))\times P3\times(r^2-a^2)^2$. Because of this, in the valve 201, like in the above-described valve, when the pressure P2 in each of the lower valve chambers 231 and 232 is higher than the pressure P1 in each of the upper valve chambers 233 and 234 and lower than the provided pressure P3, the diaphragm 120 is in contact with the valve seat 139 and closes the third vent hole 113; when the pressure P2 in each of the lower valve chambers 231 and 232 is equal to or higher than the provided pressure P3, the diaphragm 120 is separated from the valve seat 138.

Then, when the piezoelectric pump 10 is deactivated and the pressure P2 in each of the lower valve chambers 231 and 232 becomes equal to or lower than the pressure P1 in each of the upper valve chambers 233 and 234, the diaphragm 120 returns to the state where it is separated from the valve seat 139 and is in contact with the valve seat 138 illustrated in FIG. 11.

Accordingly, the valve 201 can offer substantially the same advantages as those in the valve 101. The sphygmomanometer device 200 including the valve 201 can also provide substantially the same advantages as those in the sphygmomanometer device 100.

A sphygmomanometer device 300 according to a third embodiment of the present disclosure is described below.

Figure 12:
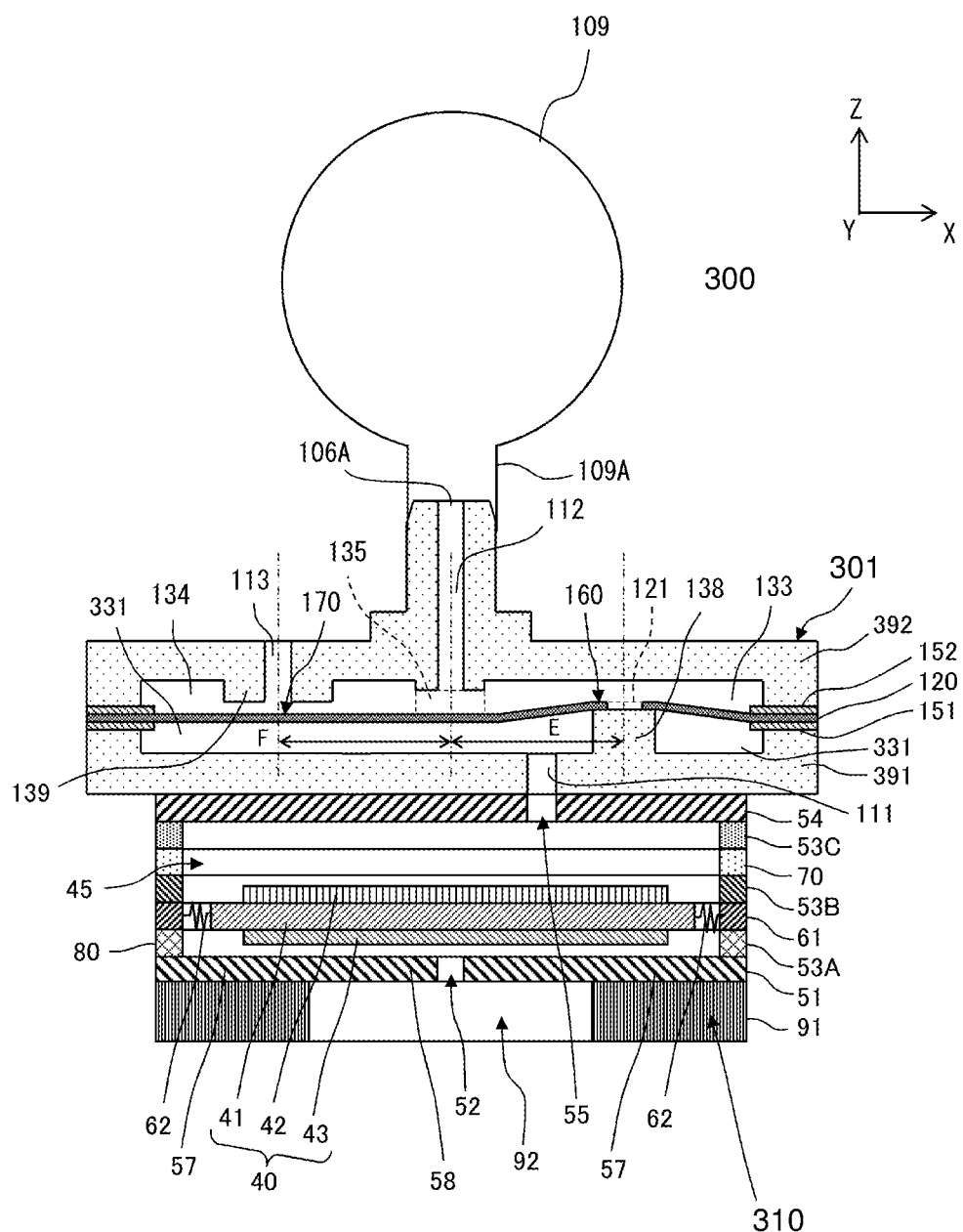
FIG. 12 is a cross-sectional view of a main portion in a sphygmomanometer device 300 according to a third embodiment of the present disclosure.

FIG. 12 is a cross-sectional view of a main portion in the sphygmomanometer device 300 according to the third embodiment of the present disclosure.

The sphygmomanometer device 300 differs from the sphygmomanometer device 100 in a first valve housing 391 and a piezoelectric pump 310 included in a valve 301.

The first valve housing 391 in the valve 301 differs from the first valve housing 191 in the valve 101 in that it does not include a wall portion 185 being a partition between the lower valve chamber 132 and lower valve chamber 131 or the first vent hole 110 (see FIGS. 1 and 3). Because of this, in the valve 301, the center of the diaphragm 120 is most displaced.

The piezoelectric pump 310 also differs from the piezoelectric pump 10 in that it does not include the discharge hole 56.

The other configurations are the same, and the description thereof is omitted.

In the valve 301, the distance F between the central axis of the third vent hole 113 surrounded by the valve seat 139 and the central axis of the diaphragm 120 is shorter than the distance E between the central axis of the opening portion 121 in contact with the valve seat 138 and the central axis of the diaphragm 120. Because of this, a location on the central axis of the third vent hole 113 in the diaphragm 120 in the valve 301 is more displaced than the center of the opening portion 121.

With this structure, the valve 301 satisfies the relationship $y<3/16\times((1-v^2)/(E\times t^3))\times P3\times(r^2-a^2)^2$. Because of this, in the valve 301, like in the above-described valves, when the pressure P2 in the lower valve chamber 331 is higher than the pressure P1 in each of the upper valve chambers 133 and 134 and lower than the provided pressure P3, the diaphragm 120 is in contact with the valve seat 139 and closes the third vent hole 113; when the pressure P2 in the lower valve chamber 331 is equal to or higher than the provided pressure P3, the diaphragm 120 is separated from the valve seat 138.

Then, when the piezoelectric pump 310 is deactivated and the pressure P2 in the lower valve chamber 331 becomes equal to or lower than the pressure P1 in each of the upper valve chambers 133 and 134, the diaphragm 120 returns to the state where it is separated from the valve seat 139 and is in contact with the valve seat 138 illustrated in FIG. 12.

Accordingly, the valve 301 can offer substantially the same advantages as those in the valve 101. The sphygmomanometer device 300 including the valve 301 can also provide substantially the same advantages as those in the sphygmomanometer device 100.

A sphygmomanometer device 400 according to a fourth embodiment of the present disclosure is described below.

Figure 13:
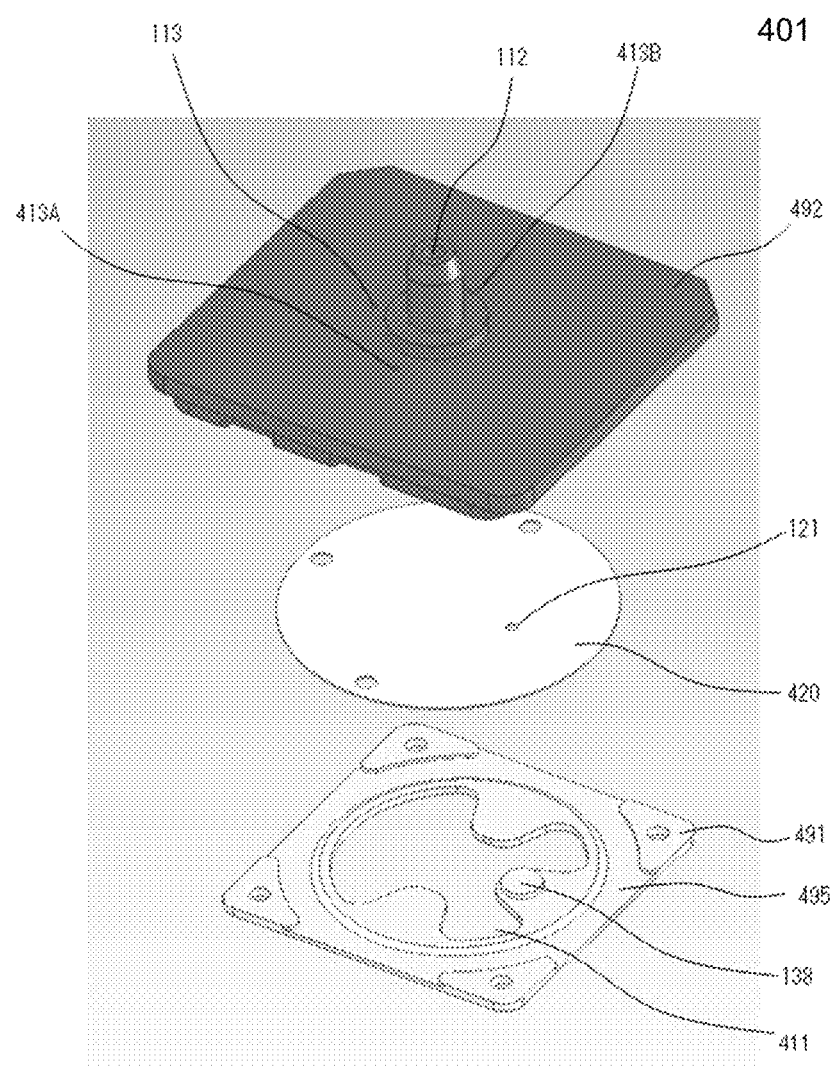
FIG. 13 is an external perspective view of a valve 401 included in a sphygmomanometer device 400 according to a fourth embodiment of the present disclosure.
Figure 14:
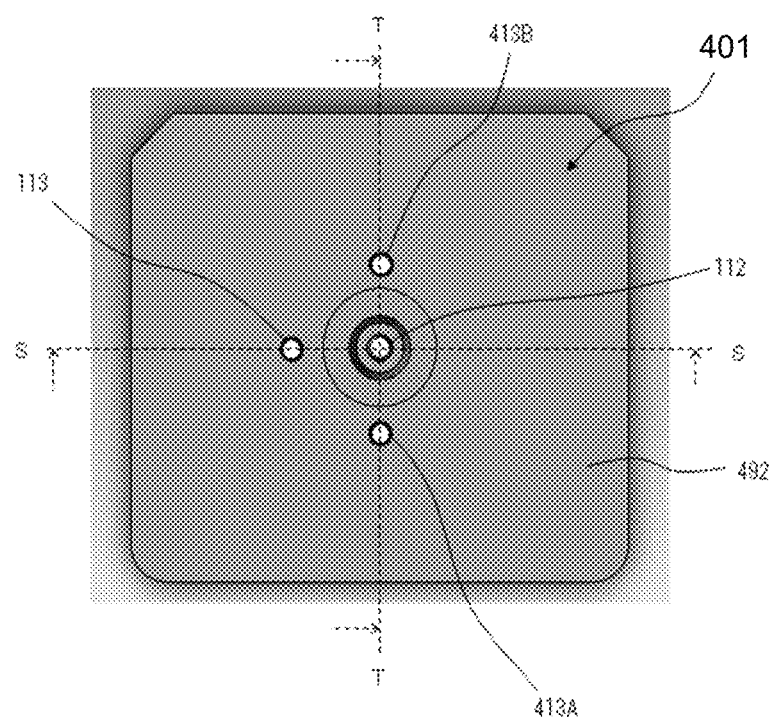
FIG. 14 is a front view of a second valve housing 492 illustrated in FIG. 13.
Figure 15:
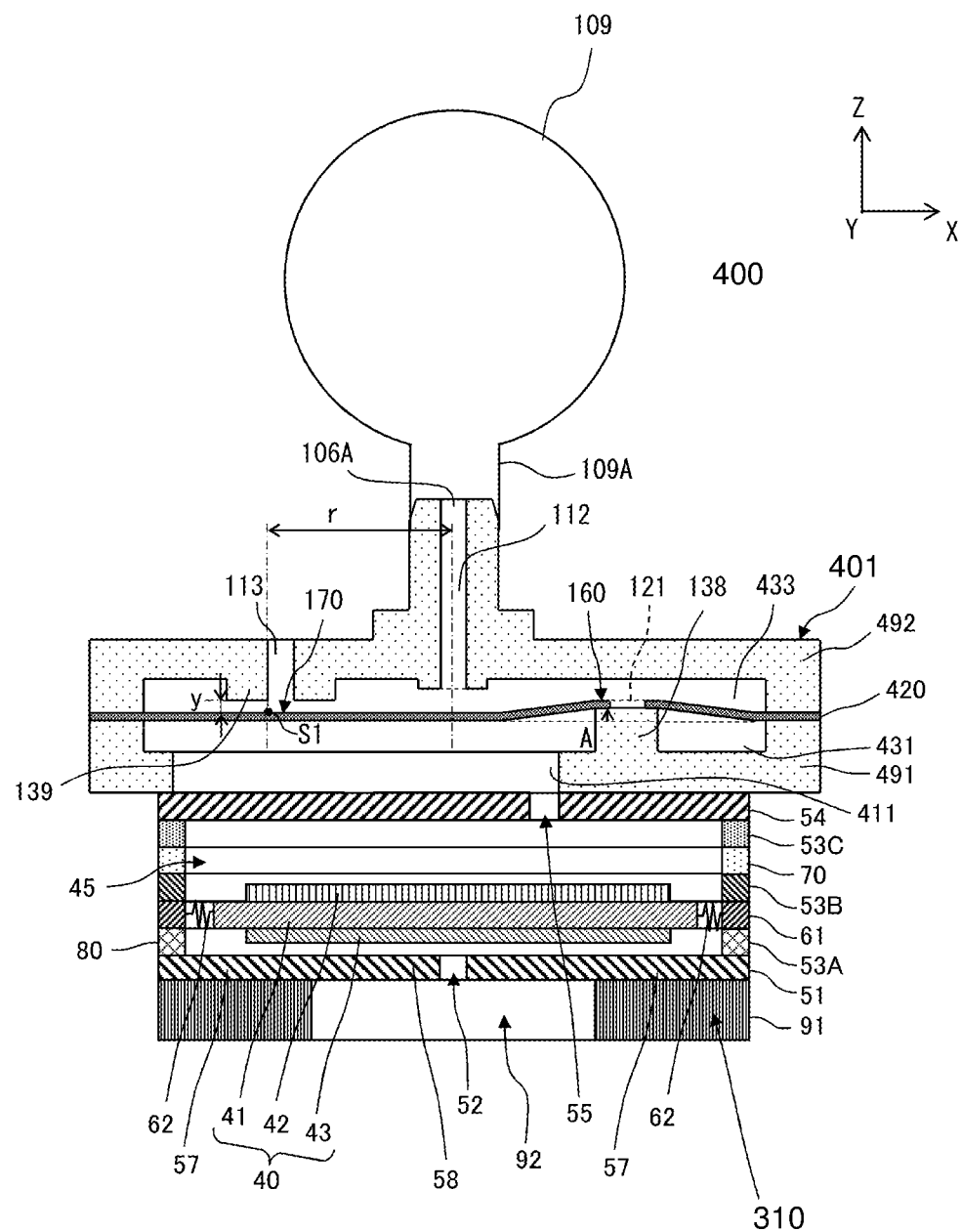
FIG. 15 is a cross-sectional view taken along line S-S illustrated in FIG. 14.
Figure 16:
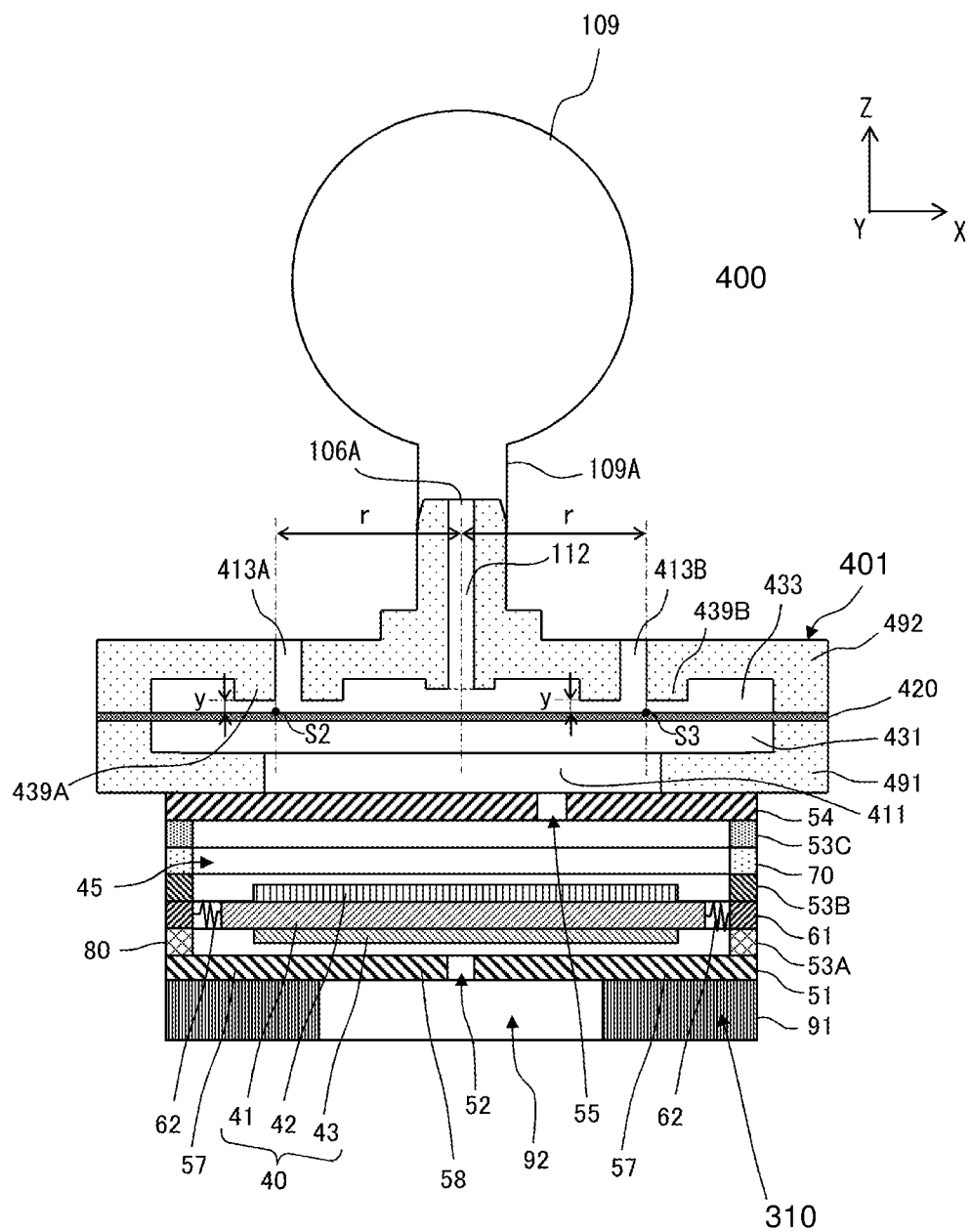
FIG. 16 is a cross-sectional view taken along line T-T illustrated in FIG. 14.

FIG. 13 is an external perspective view of a valve 401 included in the sphygmomanometer device 400 according to the fourth embodiment of the present disclosure. FIG. 14 is a front view of a second valve housing 492 illustrated in FIG. 13. FIG. 15 is a cross-sectional view taken along line S-S illustrated in FIG. 14. FIG. 16 is a cross-sectional view taken along line T-T illustrated in FIG. 14. In the cross sections in FIGS. 14 and 15, not only the valve 401, but also the sphygmomanometer device 400 is generally illustrated.

The main points of difference between the sphygmomanometer device 400 and the sphygmomanometer device 100 are a first valve housing 491, the second valve housing 492, and a diaphragm 420 included in the valve 401.

The first valve housing 491 in the valve 401 differs from the first valve housing 191 in the valve 101 in that it does not include the wall portion 185 being the partition between the lower valve chamber 132 and lower valve chamber 131 or the first vent hole 110 (see FIGS. 1 and 3), as illustrated in FIGS. 14 to 16. The first valve housing 491 has a first vent hole 411. Because of this, in the valve 401, the center of the diaphragm 420 is most displaced.

The second valve housing 492 in the valve 401 differs from the second valve housing 192 in the valve 101 in that it includes third vent holes 413A and 413B and valve seats 439A and 439B, as illustrated in FIGS. 13, 14, and 16. Each of the valve seats 439A and 439B has the same shape as that of the valve seat 139. Each of the third vent holes 413A and 413B has the same shape as that of the third vent hole 113.

That is, the second valve housing 492 has the three third vent holes 113, 413A, and 413B. The third vent holes 113, 413A, and 413B are evenly spaced apart from the central axis of the diaphragm 420. In FIG. 16, r denotes the distance from the central axis of the diaphragm 420 to the outermost peripheral point in the perimeter of each of the third vent holes 113, 413A, and 413B.

The diaphragm 420 differs from the diaphragm 120 in that it has a different shape. The diaphragm 420 has a disc shape. The diaphragm 420 is placed on a ring-shaped portion 495 in the first valve housing 491 and held between the first valve housing 491 and second valve housing 492.

That is, the diaphragm 420 is fixed to the second valve housing 492 and first valve housing 491 with an adhesive such that it is separated from the valve seats 139, 439A, and 439B and the periphery of the opening portion 121 in the diaphragm 420 is in contact with the valve seat 138 while providing a pressure thereto.

Thus, the diaphragm 420 defines a lower valve chamber 431 communicating with the first vent hole 411 and an upper valve chamber 433 communicating with the second vent hole 112 and third vent holes 113, 413A, and 413B, together with the second valve housing 492 and first valve housing 491.

The piezoelectric pump 310 also differs from the piezoelectric pump 10 in that it does not include the discharge hole 56.

The other configurations are the same, and the description thereof is omitted.

In the valve 401, the length A in which the valve seat 138 depresses the diaphragm 420 is shorter than each of the lengths y from the locations S1, S2, and S3 on the above-described peripheral point axis in the diaphragm 420 to the valve seats 139, 439A, and 439B, respectively. With this structure, the valve 401 satisfies the relationship $y < 3/16 \times ((1-v^2)/(E \times t^3)) \times P3 \times (r^2 - a^2)^2$.

Because of this, in the valve 401, like in the above-described valves, when the pressure P2 in the lower valve chamber 431 is higher than the pressure P1 in the upper valve chamber 433 and lower than the provided pressure P3, the diaphragm 420 is in contact with the valve seats 139, 439A, and 439B and closes the third vent holes 113, 413A, and 413B; when the pressure P2 in the lower valve chamber 431 is equal to or higher than the provided pressure P3, the diaphragm 420 is separated from the valve seat 138.

Then, when the piezoelectric pump 310 is deactivated and the pressure P2 in the lower valve chamber 431 becomes equal to or lower than the pressure P1 in the upper valve chamber 433, the diaphragm 420 returns to the state where it separated from the valve seats 139, 439A, and 439B and is in contact with the valve seat 138 illustrated in FIGS. 15 and 16.

Accordingly, the valve 401 can offer substantially the same advantages as those in the valve 101. In addition, because the second valve housing 492 has the plurality of third vent holes 113, 413A, and 413B, the valve 401 can achieve a shorter exhaust time than the valve 101.

The sphygmomanometer device 400 including the valve 401 can also provide substantially the same advantages.

OTHER EMBODIMENTS

Air is used as the fluid in the above-described embodiments. The fluid is not limited to the air. The fluid may be a gas other than the air.

A sphygmomanometer device is illustrated as one example of the fluid control device in the above-described embodiments. The fluid control device is not limited to the sphygmomanometer device. The fluid control device may be a device different from the sphygmomanometer device, and a container other than the cuff may be filled with a gas.

The pump in the above-described embodiments includes the unimorph actuator 40 capable of bending and vibrating. The pump may include a bimorph actuator including piezoelectric elements attached to both sides of a vibrating plate and capable of bending and vibrating.

The sphygmomanometer device in the above-described embodiments includes the piezoelectric pump 10 driven by expansion and contraction of the piezoelectric element 42. The pump is not limited to the piezoelectric type. For example, the sphygmomanometer device may include an electromagnetic pump, which is driven by electromagnetic induction.

The piezoelectric element is made of a PZT ceramic material in the above-described embodiments. The material of the piezoelectric element is not limited to the PZT ceramic material. The piezoelectric element may be made of another piezoelectric material, such as a non-lead piezoelectric ceramic material, for example, a potassium sodium niobate ceramic material or an alkali niobate ceramic material.

The valve 101 in the above-described embodiment includes the first seal member 151 (see FIG. 1), in which the perimeter of the first through hole 155A is smaller than that of the lower valve chamber 131 and the perimeter of the first through hole 155B is smaller than that of the lower valve chamber 132. The first seal member is not limited to that member. For example, it may include a first seal member in which the perimeter of the first through hole 155A is equal to that of the lower valve chamber 131 and the perimeter of the first through hole 155B is equal to that of the lower valve chamber 132.

Similarly, the valve 101 in the above-described embodiment includes the second seal member 152 (see FIG. 2), in which the perimeter of the second through hole 156A is smaller than that of the upper valve chamber 133 and the perimeter of the second through hole 156B is smaller than that of the upper valve chamber 134. The second seal member is not limited to that member. For example, it may include a second seal member in which the perimeter of the second through hole 156A is equal to that of the upper valve chamber 133 and the perimeter of the second through hole 156B is equal to that of the upper valve chamber 134.

Finally, it should be considered that the description of the above-described embodiments is merely an example in all points and non-limiting. The scope of the present invention is defined not by the above-described embodiments but by the appended claims of the invention. Further, the scope of the present invention is intended to encompass meanings equivalent to the appended claims of the invention and all the modifications within the scope of the present invention.

REFERENCE SIGNS LIST 10 piezoelectric pump
40 piezoelectric actuator
41 vibrating plate
42 piezoelectric element
43 reinforcement
45 pump chamber
51 flexible plate
52 suction hole
53A to 53C spacer
54 cover plate
55 discharge hole
56 discharge hole
57 fixed portion
58 movable portion
60 vibrating plate unit
61 frame plate
62 coupling portion
63 outer terminal
70 electrode conductive plate
71 frame member
72 outer terminal
73 inner terminal
80 pump housing
91 substrate
92 opening portion
100 sphygmomanometer device
101 valve
106A cuff connection port
109 cuff
109A cuff rubber tube
110, 111 first vent hole
112 second vent hole
113 third vent hole
120 diaphragm
121 opening portion
131, 132 lower valve chamber
133, 134 upper valve chamber
135 communication path
138, 139 valve seat
151 first seal member
152 second seal member
155A to 155C first through hole
156A to 156C second through hole
160 check valve
170 exhaust valve
180 first protruding portion
181 second protruding portions
182 opening portion
185 wall portion
191 first valve housing
192 second valve housing
200 sphygmomanometer device
201 valve
231, 232 lower valve chamber
233, 234 upper valve chamber
291 first valve housing
292 second valve housing
300 sphygmomanometer device
301 valve
310 piezoelectric pump
391 first valve housing
400 sphygmomanometer device
401 valve
411 first vent hole
413A, 413B third vent hole
420 diaphragm
431 lower valve chamber
433 upper valve chamber
439A, 439B valve seat
491 first valve housing
492 second valve housing
900 fluid control device
901 valve
910, 911 first vent hole
912 second vent hole
913 third vent hole
920 diaphragm
921 opening portion
931, 932 lower valve chamber
933, 934 upper valve chamber
938, 939 valve seat
991 first valve housing
992 second valve housing

The invention claimed is:

1. A valve comprising:
a valve housing having a first vent hole, a second vent hole, a third vent hole, a first valve seat, and a second valve seat, the second valve seat protruding from a periphery of the third vent hole; and
a diaphragm having an opening portion and fixed to the valve housing such that a periphery of the opening portion is in contact with the first valve seat while providing a pressure thereto and the diaphragm is separated from the second valve seat,
wherein the diaphragm defines a first valve chamber communicating with the first vent hole and a second valve chamber communicating with the second vent hole and the third vent hole, together with the valve housing, and
when a pressure in the first valve chamber and the second valve chamber are equal, the diaphragm is separated from the second valve seat, when the pressure in the first valve chamber is higher than the pressure in the second valve chamber and lower than the provided pressure, the diaphragm is in contact with the second valve seat and closes the third vent hole, and when the pressure in the first valve chamber is equal to or higher than the provided pressure, the diaphragm is separated from the first valve seat.

2. The valve according to claim 1, wherein when the pressure in the first valve chamber is equal to or lower than the pressure in the second valve chamber, the diaphragm is separated from the second valve seat, opens the third vent hole, and is in contact with the first valve seat.

3. The valve according to claim 1, wherein a relationship $y<3/16\times((1-v^2)/(E\times t^3))\times P3\times(r^2-a^2)^2$ is satisfied, where E denotes a Young's modulus of the diaphragm, v denotes a Poisson's ratio of the diaphragm, a denotes a radius of a portion receiving the pressure in the first valve chamber in the diaphragm, t denotes a thickness of the diaphragm, r denotes a distance from a central axis of the diaphragm to an outermost peripheral point in a perimeter of the third vent hole, P3 denotes the provided pressure, and y denotes a distance from a location on a peripheral point axis in the diaphragm to the second valve seat.

4. A fluid control device comprising:
a pump having a discharge hole;
the valve according to claim 1; and
a container configured to store fluid,
wherein the first vent hole in the valve is connected to the discharge hole in the pump, and
the second vent hole in the valve is connected to the container.

5. A sphygmomanometer comprising the fluid control device according to claim 4.

6. The valve according to claim 2, wherein a relationship $y<3/16\times((1-v^2)/(E\times t^3))\times P3\times(r^2-a^2)^2$ is satisfied, where E denotes a Young's modulus of the diaphragm, v denotes a Poisson's ratio of the diaphragm, a denotes a radius of a portion receiving the pressure in the first valve chamber in the diaphragm, t denotes a thickness of the diaphragm, r denotes a distance from a central axis of the diaphragm to an outermost peripheral point in a perimeter of the third vent hole, P3 denotes the provided pressure, and y denotes a distance from a location on a peripheral point axis in the diaphragm to the second valve seat.

7. A fluid control device comprising:
a pump having a discharge hole;
the valve according to claim 2; and
a container configured to store fluid,
wherein the first vent hole in the valve is connected to the discharge hole in the pump, and
the second vent hole in the valve is connected to the container.

8. A fluid control device comprising:
a pump having a discharge hole;
the valve according to claim 3; and
a container configured to store fluid,
wherein the first vent hole in the valve is connected to the discharge hole in the pump, and
the second vent hole in the valve is connected to the container.

* * * * *